(12) United States Patent
Yee et al.

(10) Patent No.: US 10,952,891 B1
(45) Date of Patent: Mar. 23, 2021

(54) TREATMENT SYSTEMS WITH ADJUSTABLE GAP APPLICATORS AND METHODS FOR COOLING TISSUE

(71) Applicant: Zeltiq Aesthetics, Inc., Pleasanton, CA (US)

(72) Inventors: Peter Yee, San Ramon, CA (US); George Frangineas, Jr., Fremont, CA (US); Kerrie Jiang, Pleasanton, CA (US); Bryan J. Weber, Livermore, CA (US)

(73) Assignee: Zeltiq Aesthetics, Inc., Pleasanton, CA (US)

( * ) Notice: Subject to any disclaimer, the term of this patent is extended or adjusted under 35 U.S.C. 154(b) by 314 days.

(21) Appl. No.: 14/710,407

(22) Filed: May 12, 2015

Related U.S. Application Data

(60) Provisional application No. 61/992,813, filed on May 13, 2014.

(51) Int. Cl.
*A61F 7/00* (2006.01)
*A61B 19/00* (2006.01)

(52) U.S. Cl.
CPC ............... *A61F 7/00* (2013.01); *A61B 19/00* (2013.01); *A61F 7/007* (2013.01); *A61F 2007/0056* (2013.01); *A61F 2007/0075* (2013.01)

(58) Field of Classification Search
CPC .... A61F 7/00; A61F 7/007; A61F 2007/0075; A61F 2007/0056; A61B 19/00
See application file for complete search history.

(56) References Cited

U.S. PATENT DOCUMENTS

| | | | |
|---|---|---|---|
| 681,806 | A | 9/1901 | Mignault et al. |
| 889,810 | A | 6/1908 | Robinson et al. |
| 1,093,868 | A | 4/1914 | Leighty |
| 2,516,491 | A | 7/1950 | Swastek |
| 2,521,780 | A | 9/1950 | Dodd et al. |
| 2,726,658 | A | 12/1955 | Chessey |
| 2,766,619 | A | 10/1956 | Tribus et al. |

(Continued)

FOREIGN PATENT DOCUMENTS

| | | |
|---|---|---|
| AU | 2011253768 A1 | 6/2012 |
| CA | 2441489 A1 | 3/2005 |

(Continued)

OTHER PUBLICATIONS

"ThermaCool Monopolar Capacitive Radiofrequency, The one choice for nonablative tissue tightening and contouring", Thermage, Inc. Tech Brochure, Nov. 30, 2005, 8 pgs.

(Continued)

*Primary Examiner* — Kaitlyn E Smith
*Assistant Examiner* — Yasamin Ekrami
(74) *Attorney, Agent, or Firm* — Perkins Coie LLP

(57) ABSTRACT

A system for treating a subject can include an adjustable vacuum applicator configured to receive the subject's tissue by applying a vacuum. The vacuum applicator can have an cavity adjustment mechanism with different modes for widening and narrowing a tissue-receiving cavity to adjust the thermal contact between the vacuum applicator and the subject's tissue within the applicator. Sidewalls of the vacuum applicator can be moved to positive draft angle positions to help draw tissue deeper into the tissue-receiving cavity.

25 Claims, 12 Drawing Sheets

(56) References Cited

U.S. PATENT DOCUMENTS

| | | |
|---|---|---|
| 2,851,602 A | 9/1958 | Cramwinckel et al. |
| 3,093,135 A | 6/1963 | Hirschhorn |
| 3,132,688 A | 5/1964 | Nowak |
| 3,133,539 A | 5/1964 | Wiiliam et al. |
| 3,282,267 A | 11/1966 | Eidus |
| 3,502,080 A | 3/1970 | Hirschhorn |
| 3,587,577 A | 6/1971 | Zubkov et al. |
| 3,591,645 A | 7/1971 | Selwitz |
| 3,692,338 A | 9/1972 | Nick |
| 3,703,897 A | 11/1972 | Mack et al. |
| 3,710,784 A | 1/1973 | Taylor |
| 3,786,814 A | 1/1974 | Armao |
| 3,827,436 A | 8/1974 | Andera et al. |
| 3,942,519 A | 3/1976 | Shock |
| 3,948,269 A | 4/1976 | Zimmer |
| 3,986,385 A | 10/1976 | Johnston et al. |
| 3,993,053 A | 11/1976 | Grossan |
| 4,002,221 A | 1/1977 | Buchalter |
| 4,026,299 A | 5/1977 | Sauder |
| 4,140,130 A | 2/1979 | Storm |
| 4,149,529 A | 4/1979 | Copeland et al. |
| 4,178,429 A | 12/1979 | Scheffer |
| 4,202,336 A | 5/1980 | Van Gerven |
| 4,266,043 A | 5/1981 | Fujii et al. |
| 4,269,068 A | 5/1981 | Molina |
| 4,381,009 A | 4/1983 | Del Bon |
| 4,396,011 A | 8/1983 | Mack et al. |
| 4,459,854 A | 7/1984 | Richardson et al. |
| 4,470,263 A | 9/1984 | Lehovec et al. |
| 4,483,341 A | 11/1984 | Witteles |
| 4,528,979 A | 7/1985 | Marchenko et al. |
| 4,531,524 A | 7/1985 | Mioduski |
| 4,548,212 A | 10/1985 | Leung |
| 4,555,313 A | 11/1985 | Duchane et al. |
| 4,585,002 A | 4/1986 | Kissin |
| 4,603,076 A | 7/1986 | Bowditch et al. |
| 4,614,191 A | 9/1986 | Perler et al. |
| 4,644,955 A | 2/1987 | Mioduski |
| 4,664,110 A | 5/1987 | Schanzlin |
| 4,700,701 A | 10/1987 | Montaldi |
| 4,718,429 A | 1/1988 | Smidt |
| 4,741,338 A | 5/1988 | Miyamae |
| 4,758,217 A | 7/1988 | Gueret |
| 4,764,463 A | 8/1988 | Mason et al. |
| 4,802,475 A | 2/1989 | Weshahy |
| 4,832,022 A | 5/1989 | Tjulkov et al. |
| 4,846,176 A | 7/1989 | Golden |
| 4,850,340 A | 7/1989 | Onishi |
| 4,869,250 A | 9/1989 | Bitterly |
| 4,880,564 A | 11/1989 | Abel et al. |
| 4,905,697 A | 3/1990 | Heggs et al. |
| 4,906,463 A | 3/1990 | Cleary et al. |
| 4,930,317 A | 6/1990 | Klein |
| 4,935,345 A | 6/1990 | Guilbeau et al. |
| 4,961,422 A | 10/1990 | Marchosky et al. |
| 4,962,761 A | 10/1990 | Golden |
| 4,990,144 A | 2/1991 | Blott et al. |
| 5,007,433 A | 4/1991 | Hermsdoerffer et al. |
| 5,018,521 A | 5/1991 | Campbell et al. |
| 5,024,650 A | 6/1991 | Hagiwara et al. |
| 5,065,752 A | 11/1991 | Sessions et al. |
| 5,069,208 A | 12/1991 | Noppel et al. |
| 5,084,671 A | 1/1992 | Miyata et al. |
| 5,108,390 A | 4/1992 | Potocky et al. |
| 5,119,674 A | 6/1992 | Nielsen |
| 5,139,496 A | 8/1992 | Hed |
| 5,143,063 A | 9/1992 | Fellner |
| 5,148,804 A | 9/1992 | Hill et al. |
| 5,158,070 A | 10/1992 | Dory |
| 5,169,384 A | 12/1992 | Bosniak et al. |
| 5,197,466 A | 3/1993 | Marchosky et al. |
| 5,207,674 A | 5/1993 | Hamilton |
| 5,221,726 A | 6/1993 | Dabi et al. |
| 5,264,234 A | 11/1993 | Windhab et al. |
| 5,277,030 A | 1/1994 | Miller |
| 5,314,423 A | 5/1994 | Seney et al. |
| 5,327,886 A | 7/1994 | Chiu |
| 5,330,745 A | 7/1994 | Mcdow et al. |
| 5,333,460 A | 8/1994 | Lewis et al. |
| 5,334,131 A | 8/1994 | Omandam et al. |
| 5,336,616 A | 8/1994 | Livesey et al. |
| 5,339,541 A | 8/1994 | Owens |
| 5,342,617 A | 8/1994 | Gold et al. |
| 5,351,677 A | 10/1994 | Kami et al. |
| 5,358,467 A | 10/1994 | Milstein et al. |
| 5,362,966 A | 11/1994 | Rosenthal et al. |
| 5,363,347 A | 11/1994 | Nguyen |
| 5,372,608 A | 12/1994 | Johnson |
| 5,386,837 A | 2/1995 | Sterzer |
| 5,411,541 A | 5/1995 | Bell et al. |
| 5,427,772 A | 6/1995 | Hagan et al. |
| 5,433,717 A | 7/1995 | Rubinsky et al. |
| 5,456,703 A | 10/1995 | Beeuwkes, III et al. |
| 5,472,416 A | 12/1995 | Blugerman et al. |
| 5,486,207 A | 1/1996 | Mahawili |
| 5,497,596 A | 3/1996 | Zatkulak |
| 5,501,655 A | 3/1996 | Rolt et al. |
| 5,505,726 A | 4/1996 | Meserol |
| 5,505,730 A | 4/1996 | Edwards et al. |
| 5,507,790 A | 4/1996 | Weiss |
| 5,514,105 A | 5/1996 | Goodman, Jr. et al. |
| 5,514,170 A | 5/1996 | Mauch |
| 5,516,505 A | 5/1996 | McDow |
| 5,531,742 A | 7/1996 | Barken |
| 5,562,604 A | 10/1996 | Yablon et al. |
| 5,571,801 A | 11/1996 | Segall et al. |
| 5,575,812 A | 11/1996 | Owens et al. |
| 5,603,221 A | 2/1997 | Maytal |
| 5,628,769 A | 5/1997 | Saringer |
| 5,634,890 A | 6/1997 | Morris |
| 5,634,940 A | 6/1997 | Panyard |
| 5,647,051 A | 7/1997 | Neer |
| 5,647,868 A | 7/1997 | Chinn |
| 5,650,450 A | 7/1997 | Lovette et al. |
| 5,651,773 A | 7/1997 | Perry et al. |
| 5,654,279 A | 8/1997 | Rubinsky et al. |
| 5,654,546 A | 8/1997 | Lindsay et al. |
| 5,660,836 A | 8/1997 | Knowlton et al. |
| 5,665,053 A | 9/1997 | Jacobs |
| 5,672,172 A | 9/1997 | Zupkas |
| 5,700,284 A | 12/1997 | Owens et al. |
| 5,725,483 A | 3/1998 | Podolsky |
| 5,733,280 A | 3/1998 | Avitall |
| 5,741,248 A | 4/1998 | Stern et al. |
| 5,746,702 A | 5/1998 | Gelfgat et al. |
| 5,746,736 A | 5/1998 | Tankovich |
| 5,755,663 A | 5/1998 | Larsen et al. |
| 5,755,753 A | 5/1998 | Knowlton et al. |
| 5,755,755 A | 5/1998 | Panyard |
| 5,759,182 A | 6/1998 | Varney et al. |
| 5,759,764 A | 6/1998 | Polovina et al. |
| 5,769,879 A | 6/1998 | Richards et al. |
| 5,785,955 A | 7/1998 | Fischer |
| 5,792,080 A | 8/1998 | Ookawa et al. |
| 5,800,490 A | 9/1998 | Patz et al. |
| 5,814,040 A | 9/1998 | Nelson et al. |
| 5,817,050 A | 10/1998 | Klein et al. |
| 5,817,149 A | 10/1998 | Owens et al. |
| 5,817,150 A | 10/1998 | Owens et al. |
| 5,830,208 A | 11/1998 | Muller et al. |
| 5,833,685 A | 11/1998 | Tortal et al. |
| 5,844,013 A | 12/1998 | Kenndoff et al. |
| 5,865,841 A | 2/1999 | Kolen et al. |
| 5,871,524 A | 2/1999 | Knowlton |
| 5,871,526 A | 2/1999 | Gibbs et al. |
| 5,885,211 A | 3/1999 | Eppstein et al. |
| 5,891,617 A | 4/1999 | Watson et al. |
| 5,895,418 A | 4/1999 | Saringer |
| 5,901,707 A | 5/1999 | Goncalves |
| 5,902,256 A | 5/1999 | Benaron |
| 5,919,219 A | 7/1999 | Knowlton et al. |
| 5,944,748 A | 8/1999 | Mager et al. |
| 5,948,011 A | 9/1999 | Knowlton et al. |
| 5,954,680 A | 9/1999 | Augustine et al. |

(56) References Cited

U.S. PATENT DOCUMENTS

| | | | |
|---|---|---|---|
| 5,964,092 A | 10/1999 | Tozuka et al. |
| 5,964,749 A | 10/1999 | Eckhouse et al. |
| 5,967,976 A | 10/1999 | Larsen et al. |
| 5,980,561 A | 11/1999 | Kolen et al. |
| 5,986,167 A | 11/1999 | Arteman et al. |
| 5,989,286 A | 11/1999 | Owens et al. |
| 5,997,530 A | 12/1999 | Nelson et al. |
| 6,017,337 A | 1/2000 | Pira |
| 6,023,932 A | 2/2000 | Johnston |
| 6,032,675 A | 3/2000 | Rubinsky |
| 6,039,694 A | 3/2000 | Larson et al. |
| 6,041,787 A | 3/2000 | Rubinsky |
| 6,047,215 A | 4/2000 | McClure et al. |
| 6,049,927 A | 4/2000 | Thomas et al. |
| 6,051,159 A | 4/2000 | Hao et al. |
| 6,071,239 A | 6/2000 | Cribbs et al. |
| 6,074,415 A | 6/2000 | Der Ovanesian |
| 6,093,230 A | 7/2000 | Johnson et al. |
| 6,102,885 A | 8/2000 | Bass |
| 6,104,952 A | 8/2000 | Tu et al. |
| 6,104,959 A | 8/2000 | Spertell et al. |
| 6,106,517 A | 8/2000 | Zupkas |
| 6,113,558 A | 9/2000 | Rosenschein et al. |
| 6,113,559 A | 9/2000 | Klopotek |
| 6,113,626 A | 9/2000 | Clifton et al. |
| 6,120,519 A | 9/2000 | Weber et al. |
| 6,139,544 A | 10/2000 | Mikus et al. |
| 6,150,148 A | 11/2000 | Nanda et al. |
| 6,151,735 A | 11/2000 | Koby et al. |
| 6,152,952 A | 11/2000 | Owens et al. |
| 6,171,301 B1 | 1/2001 | Nelson et al. |
| 6,180,867 B1 | 1/2001 | Hedengren et al. |
| 6,226,996 B1 | 5/2001 | Weber et al. |
| 6,241,753 B1 | 6/2001 | Knowlton |
| 6,264,649 B1 | 7/2001 | Whitcroft et al. |
| 6,273,884 B1 | 8/2001 | Altshuler et al. |
| 6,290,988 B1 | 9/2001 | Van Vilsteren et al. |
| 6,311,090 B1 | 10/2001 | Knowlton |
| 6,311,497 B1 | 11/2001 | Chung |
| 6,312,453 B1 | 11/2001 | Stefanile et al. |
| 6,350,276 B1 | 2/2002 | Knowlton |
| 6,354,297 B1 | 3/2002 | Eiseman |
| 6,357,907 B1 | 3/2002 | Cleveland et al. |
| 6,375,673 B1 | 4/2002 | Clifton et al. |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,401,722 B1 | 6/2002 | Krag |
| 6,405,090 B1 | 6/2002 | Knowlton |
| 6,413,255 B1 | 7/2002 | Stern |
| 6,425,912 B1 | 7/2002 | Knowlton |
| 6,426,445 B1 | 7/2002 | Young et al. |
| 6,430,446 B1 | 8/2002 | Knowlton |
| 6,430,956 B1 | 8/2002 | Haas et al. |
| 6,438,424 B1 | 8/2002 | Knowlton |
| 6,438,954 B1 | 8/2002 | Goetz et al. |
| 6,438,964 B1 | 8/2002 | Giblin |
| 6,453,202 B1 | 9/2002 | Knowlton |
| 6,458,888 B1 | 10/2002 | Hood et al. |
| 6,461,378 B1 | 10/2002 | Knowlton |
| 6,470,216 B1 | 10/2002 | Knowlton |
| 6,471,693 B1 | 10/2002 | Carroll et al. |
| 6,475,211 B2 | 11/2002 | Chess et al. |
| 6,478,811 B1 | 11/2002 | Dobak, III et al. |
| 6,494,844 B1 | 12/2002 | Van Bladel et al. |
| 6,497,721 B2 | 12/2002 | Ginsburg et al. |
| 6,508,831 B1 | 1/2003 | Kushnir |
| 6,514,244 B2 | 2/2003 | Pope et al. |
| 6,519,964 B2 | 2/2003 | Bieberich |
| 6,523,354 B1 | 2/2003 | Tolbert |
| 6,527,765 B2 | 3/2003 | Kelman et al. |
| 6,527,798 B2 | 3/2003 | Ginsburg et al. |
| 6,544,248 B1 | 4/2003 | Bass |
| 6,547,811 B1 | 4/2003 | Becker et al. |
| 6,548,297 B1 | 4/2003 | Kuri-Harcuch et al. |
| 6,551,255 B2 | 4/2003 | Van Bladel et al. |
| 6,551,341 B2 | 4/2003 | Boylan et al. |
| 6,551,348 B1 | 4/2003 | Blalock et al. |
| 6,551,349 B2 | 4/2003 | Lasheras et al. |
| 6,569,189 B1 | 5/2003 | Augustine et al. |
| 6,585,652 B2 | 7/2003 | Lang et al. |
| 6,592,577 B2 | 7/2003 | Abboud et al. |
| 6,605,080 B1 | 8/2003 | Altshuler et al. |
| 6,607,498 B2 | 8/2003 | Eshel |
| 6,620,187 B2 | 9/2003 | Carson et al. |
| 6,620,188 B1 | 9/2003 | Ginsburg et al. |
| 6,620,189 B1 | 9/2003 | Machold et al. |
| 6,623,430 B1 | 9/2003 | Slayton et al. |
| 6,626,854 B2 | 9/2003 | Friedman et al. |
| 6,632,219 B1 | 10/2003 | Baranov et al. |
| 6,635,053 B1 | 10/2003 | Lalonde et al. |
| 6,643,535 B2 | 11/2003 | Damasco et al. |
| 6,645,162 B2 | 11/2003 | Friedman et al. |
| 6,645,229 B2 | 11/2003 | Matsumura et al. |
| 6,645,232 B2 | 11/2003 | Carson |
| 6,648,904 B2 | 11/2003 | Altshuler et al. |
| 6,656,208 B2 | 12/2003 | Grahn et al. |
| 6,660,027 B2 | 12/2003 | Gruszecki et al. |
| 6,662,054 B2 | 12/2003 | Kreindel et al. |
| 6,682,550 B2 | 1/2004 | Clifton et al. |
| 6,685,731 B2 | 2/2004 | Kushnir et al. |
| 6,694,170 B1 | 2/2004 | Mikus et al. |
| 6,695,874 B2 | 2/2004 | Machold et al. |
| 6,697,670 B2 | 2/2004 | Chornenky |
| 6,699,237 B2 | 3/2004 | Weber et al. |
| 6,699,266 B2 | 3/2004 | Lachenbruch et al. |
| 6,699,267 B2 | 3/2004 | Voorhees et al. |
| 6,718,785 B2 | 4/2004 | Bieberich |
| 6,741,895 B1 | 5/2004 | Gafni et al. |
| 6,743,222 B2 | 6/2004 | Durkin et al. |
| 6,746,474 B2 | 6/2004 | Saadat |
| 6,749,624 B2 | 6/2004 | Knowlton |
| 6,764,493 B1 | 7/2004 | Weber et al. |
| 6,764,502 B2 | 7/2004 | Bieberich |
| 6,789,545 B2 | 9/2004 | Littrup et al. |
| 6,795,728 B2 | 9/2004 | Chornenky et al. |
| 6,820,961 B2 | 11/2004 | Johnson |
| 6,821,274 B2 | 11/2004 | McHale et al. |
| 6,840,955 B2 | 1/2005 | Ein |
| 6,849,075 B2 | 2/2005 | Bertolero et al. |
| 6,878,144 B2 | 4/2005 | Altshuler et al. |
| 6,889,090 B2 | 5/2005 | Kreindel |
| 6,892,099 B2 | 5/2005 | Jaafar et al. |
| 6,904,956 B2 | 6/2005 | Noel |
| 6,918,903 B2 | 7/2005 | Bass |
| 6,927,316 B1 | 8/2005 | Faries, Jr. et al. |
| 6,942,022 B2 | 9/2005 | Blangetti et al. |
| 6,945,942 B2 | 9/2005 | Van Bladel et al. |
| 6,948,903 B2 | 9/2005 | Ablabutyan et al. |
| 6,969,399 B2 | 11/2005 | Schock et al. |
| 7,005,558 B1 | 2/2006 | Johansson et al. |
| 7,006,874 B2 | 2/2006 | Knowlton et al. |
| 7,022,121 B2 | 4/2006 | Stern et al. |
| 7,037,326 B2 | 5/2006 | Lee |
| 7,054,685 B2 | 5/2006 | Dimmer et al. |
| 7,060,061 B2 | 6/2006 | Altshuler et al. |
| 7,077,858 B2 | 7/2006 | Fletcher et al. |
| 7,081,111 B2 | 7/2006 | Svaasand et al. |
| 7,083,612 B2 | 8/2006 | Littrup et al. |
| 7,096,204 B1 | 8/2006 | Chen et al. |
| 7,112,712 B1 | 9/2006 | Ancell |
| 7,115,123 B2 | 10/2006 | Knowlton et al. |
| 7,141,049 B2 | 11/2006 | Stern et al. |
| 7,183,360 B2 | 2/2007 | Daniel et al. |
| 7,189,252 B2 | 3/2007 | Krueger |
| 7,192,426 B2 | 3/2007 | Baust et al. |
| 7,204,832 B2 | 4/2007 | Altshuler et al. |
| 7,220,778 B2 | 5/2007 | Anderson et al. |
| 7,229,436 B2 | 6/2007 | Stern et al. |
| 7,258,674 B2 | 8/2007 | Cribbs et al. |
| 7,267,675 B2 | 9/2007 | Stern et al. |
| 7,276,058 B2 | 10/2007 | Altshuler et al. |

(56) References Cited

U.S. PATENT DOCUMENTS

| | | |
|---|---|---|
| 7,318,821 B2 | 1/2008 | Lalonde et al. |
| 7,331,951 B2 | 2/2008 | Eshel et al. |
| 7,347,855 B2 | 3/2008 | Eshel et al. |
| 7,367,341 B2 | 5/2008 | Anderson et al. |
| 7,532,201 B2 | 5/2009 | Quistgaard et al. |
| 7,572,268 B2 | 8/2009 | Babaev |
| 7,604,632 B2 | 10/2009 | Howlett et al. |
| 7,613,523 B2 | 11/2009 | Eggers et al. |
| 7,615,016 B2 | 11/2009 | Barthe et al. |
| 7,713,266 B2 | 5/2010 | Elkins et al. |
| 7,780,656 B2 | 8/2010 | Tankovich |
| 7,799,018 B2 | 9/2010 | Goulko |
| 7,824,437 B1 | 11/2010 | Saunders |
| 7,828,831 B1 | 11/2010 | Tanhehco et al. |
| 7,850,683 B2 | 12/2010 | Elkins et al. |
| 7,854,754 B2 | 12/2010 | Ting et al. |
| 7,862,558 B2 | 1/2011 | Elkins et al. |
| RE42,277 E | 4/2011 | Jaafar et al. |
| 7,938,824 B2 | 5/2011 | Chornenky et al. |
| 7,959,657 B1 | 6/2011 | Harsy et al. |
| 7,963,959 B2 | 6/2011 | Da Silva et al. |
| 7,967,763 B2 | 6/2011 | Deem et al. |
| 7,993,330 B2 | 8/2011 | Goulko |
| 7,998,137 B2 | 8/2011 | Elkins et al. |
| RE42,835 E | 10/2011 | Chornenky et al. |
| RE43,009 E | 12/2011 | Chornenky et al. |
| 8,133,180 B2 | 3/2012 | Slayton et al. |
| 8,133,191 B2 | 3/2012 | Rosenberg et al. |
| 8,192,474 B2 | 6/2012 | Levinson |
| 8,246,611 B2 | 8/2012 | Paithankar et al. |
| 8,275,442 B2 | 9/2012 | Allison |
| 8,285,390 B2 | 10/2012 | Levinson et al. |
| 8,333,700 B1 | 12/2012 | Barthe et al. |
| 8,337,539 B2 | 12/2012 | Ting et al. |
| 8,366,622 B2 | 2/2013 | Slayton et al. |
| 8,372,130 B2 | 2/2013 | Young et al. |
| 8,397,518 B1 | 3/2013 | Vistakula et al. |
| 8,414,631 B2 | 4/2013 | Quisenberry et al. |
| 8,433,400 B2 | 4/2013 | Prushinskaya et al. |
| 8,506,486 B2 | 8/2013 | Slayton et al. |
| 8,523,775 B2 | 9/2013 | Barthe et al. |
| 8,523,791 B2 | 9/2013 | Castel |
| 8,523,927 B2 | 9/2013 | Levinson et al. |
| 8,535,228 B2 | 9/2013 | Slayton et al. |
| 8,603,073 B2 | 12/2013 | Allison |
| 8,636,665 B2 | 1/2014 | Slayton et al. |
| 8,641,622 B2 | 2/2014 | Barthe et al. |
| 8,663,112 B2 | 3/2014 | Slayton et al. |
| 8,672,848 B2 | 3/2014 | Slayton et al. |
| 8,676,332 B2 | 3/2014 | Fahey |
| 8,690,778 B2 | 4/2014 | Slayton et al. |
| 8,690,779 B2 | 4/2014 | Slayton et al. |
| 8,690,780 B2 | 4/2014 | Slayton et al. |
| 8,702,774 B2 | 4/2014 | Baker et al. |
| 8,758,215 B2 | 6/2014 | Legendre et al. |
| 8,764,693 B1 | 7/2014 | Graham et al. |
| 8,834,547 B2 | 9/2014 | Anderson et al. |
| 2001/0005791 A1 | 6/2001 | Ginsburg et al. |
| 2001/0007952 A1 | 7/2001 | Shimizu |
| 2001/0023364 A1 | 9/2001 | Ahn |
| 2001/0031459 A1 | 10/2001 | Fahy et al. |
| 2001/0039439 A1 | 11/2001 | Elkins et al. |
| 2001/0045104 A1 | 11/2001 | Bailey, Sr. et al. |
| 2001/0047196 A1 | 11/2001 | Ginsburg et al. |
| 2002/0026226 A1 | 2/2002 | Ein |
| 2002/0032473 A1 | 3/2002 | Kushnir et al. |
| 2002/0042607 A1 | 4/2002 | Palmer et al. |
| 2002/0049483 A1 | 4/2002 | Knowlton |
| 2002/0058975 A1 | 5/2002 | Bieberich |
| 2002/0062142 A1 | 5/2002 | Knowlton |
| 2002/0068338 A1 | 6/2002 | Nanda et al. |
| 2002/0082668 A1 | 6/2002 | Ingman |
| 2002/0103520 A1 | 8/2002 | Latham |
| 2002/0107558 A1 | 8/2002 | Clifton et al. |
| 2002/0117293 A1 | 8/2002 | Campbell |
| 2002/0120315 A1 | 8/2002 | Furuno et al. |
| 2002/0128648 A1 | 9/2002 | Weber et al. |
| 2002/0151830 A1 | 10/2002 | Kahn |
| 2002/0151887 A1 | 10/2002 | Stern et al. |
| 2002/0156509 A1 | 10/2002 | Cheung |
| 2002/0188286 A1 | 12/2002 | Quijano et al. |
| 2002/0198518 A1 | 12/2002 | Mikus et al. |
| 2003/0032900 A1 | 2/2003 | Ella |
| 2003/0044764 A1 | 3/2003 | Soane et al. |
| 2003/0055414 A1 | 3/2003 | Altshuler et al. |
| 2003/0062040 A1 | 4/2003 | Lurie et al. |
| 2003/0069618 A1 | 4/2003 | Smith, III et al. |
| 2003/0077326 A1 | 4/2003 | Newton et al. |
| 2003/0077329 A1 | 4/2003 | Kipp et al. |
| 2003/0079488 A1 | 5/2003 | Bieberich |
| 2003/0100936 A1 | 5/2003 | Altshuler et al. |
| 2003/0109908 A1 | 6/2003 | Lachenbruch et al. |
| 2003/0109910 A1 | 6/2003 | Lachenbruch et al. |
| 2003/0109911 A1 | 6/2003 | Lachenbruch et al. |
| 2003/0114885 A1 | 6/2003 | Nova et al. |
| 2003/0120268 A1 | 6/2003 | Bertolero et al. |
| 2003/0125649 A1 | 7/2003 | McIntosh et al. |
| 2003/0187488 A1 | 10/2003 | Kreindel et al. |
| 2003/0199226 A1 | 10/2003 | Sommer et al. |
| 2003/0199859 A1 | 10/2003 | Altshuler et al. |
| 2003/0220594 A1 | 11/2003 | Halvorson et al. |
| 2003/0220635 A1 | 11/2003 | Knowlton et al. |
| 2003/0220674 A1* | 11/2003 | Anderson ............... A61B 5/415 607/96 |
| 2003/0236487 A1 | 12/2003 | Knowlton |
| 2004/0002705 A1 | 1/2004 | Knowlton et al. |
| 2004/0006328 A1 | 1/2004 | Anderson |
| 2004/0009936 A1 | 1/2004 | Tang et al. |
| 2004/0024437 A1 | 2/2004 | Machold et al. |
| 2004/0030332 A1 | 2/2004 | Knowlton et al. |
| 2004/0034341 A1 | 2/2004 | Altshuler et al. |
| 2004/0039312 A1 | 2/2004 | Hillstead et al. |
| 2004/0044384 A1 | 3/2004 | Leber et al. |
| 2004/0049178 A1 | 3/2004 | Abboud et al. |
| 2004/0073079 A1 | 4/2004 | Altshuler et al. |
| 2004/0074629 A1 | 4/2004 | Noel |
| 2004/0077977 A1 | 4/2004 | Ella et al. |
| 2004/0082886 A1 | 4/2004 | Timpson |
| 2004/0093042 A1 | 5/2004 | Altshuler et al. |
| 2004/0104012 A1 | 6/2004 | Zhou et al. |
| 2004/0106867 A1 | 6/2004 | Eshel et al. |
| 2004/0133251 A1 | 7/2004 | Altshuler et al. |
| 2004/0162596 A1 | 8/2004 | Altshuler et al. |
| 2004/0176667 A1 | 9/2004 | Mihai et al. |
| 2004/0186535 A1 | 9/2004 | Knowlton |
| 2004/0199226 A1 | 10/2004 | Shadduck |
| 2004/0206365 A1 | 10/2004 | Knowlton |
| 2004/0210214 A1 | 10/2004 | Knowlton |
| 2004/0210287 A1 | 10/2004 | Greene |
| 2004/0215294 A1 | 10/2004 | Littrup et al. |
| 2004/0249427 A1 | 12/2004 | Nabilsi et al. |
| 2004/0259855 A1 | 12/2004 | Anderson et al. |
| 2004/0260209 A1 | 12/2004 | Ella et al. |
| 2004/0260210 A1 | 12/2004 | Ella et al. |
| 2004/0260211 A1 | 12/2004 | Maalouf |
| 2005/0010197 A1 | 1/2005 | Lau et al. |
| 2005/0033957 A1 | 2/2005 | Enokida |
| 2005/0049526 A1 | 3/2005 | Baer |
| 2005/0049543 A1 | 3/2005 | Anderson et al. |
| 2005/0049661 A1 | 3/2005 | Koffroth |
| 2005/0113725 A1 | 5/2005 | Masuda |
| 2005/0143781 A1 | 6/2005 | Carbunaru et al. |
| 2005/0145372 A1 | 7/2005 | Noel |
| 2005/0149153 A1 | 7/2005 | Nakase et al. |
| 2005/0154314 A1 | 7/2005 | Quistgaard |
| 2005/0154431 A1 | 7/2005 | Quistgaard et al. |
| 2005/0159986 A1 | 7/2005 | Breeland et al. |
| 2005/0177075 A1* | 8/2005 | Meunier ............... A61H 9/005 601/7 |
| 2005/0182462 A1 | 8/2005 | Chornenky et al. |
| 2005/0187495 A1 | 8/2005 | Quistgaard et al. |
| 2005/0187597 A1 | 8/2005 | Vanderschuit |
| 2005/0203446 A1 | 9/2005 | Takashima |
| 2005/0215987 A1 | 9/2005 | Slatkine |

(56) References Cited

U.S. PATENT DOCUMENTS

| | | |
|---|---|---|
| 2005/0222565 A1 | 10/2005 | Manstein |
| 2005/0251117 A1 | 11/2005 | Anderson et al. |
| 2005/0251120 A1 | 11/2005 | Anderson et al. |
| 2005/0261753 A1 | 11/2005 | Littrup et al. |
| 2005/0277859 A1 | 12/2005 | Carlsmith et al. |
| 2005/0283144 A1 | 12/2005 | Shiono et al. |
| 2006/0030778 A1 | 2/2006 | Mendlein et al. |
| 2006/0035380 A1 | 2/2006 | Saint-Leger |
| 2006/0036300 A1 | 2/2006 | Kreindel |
| 2006/0041704 A1 | 2/2006 | Choi |
| 2006/0074313 A1 | 4/2006 | Slayton et al. |
| 2006/0079852 A1 | 4/2006 | Bubb et al. |
| 2006/0094988 A1 | 5/2006 | Tosaya et al. |
| 2006/0106836 A1 | 5/2006 | Masugi et al. |
| 2006/0111613 A1 | 5/2006 | Boutillette et al. |
| 2006/0122509 A1 | 6/2006 | Desilets |
| 2006/0189964 A1 | 8/2006 | Anderson et al. |
| 2006/0195168 A1 | 8/2006 | Dunbar et al. |
| 2006/0200063 A1 | 9/2006 | Munro et al. |
| 2006/0206040 A1 | 9/2006 | Greenberg et al. |
| 2006/0206110 A1 | 9/2006 | Knowlton et al. |
| 2006/0234899 A1 | 10/2006 | Nekmard et al. |
| 2006/0259102 A1 | 11/2006 | Slatkine |
| 2006/0265032 A1 | 11/2006 | Hennings et al. |
| 2006/0270745 A1 | 11/2006 | Hunt et al. |
| 2006/0293734 A1 | 12/2006 | Scott et al. |
| 2007/0010811 A1 | 1/2007 | Stern et al. |
| 2007/0010861 A1 | 1/2007 | Anderson et al. |
| 2007/0032561 A1 | 2/2007 | Lin et al. |
| 2007/0038156 A1 | 2/2007 | Rosenberg |
| 2007/0055156 A1 | 3/2007 | Desilets et al. |
| 2007/0055173 A1 | 3/2007 | DeLonzor et al. |
| 2007/0055179 A1 | 3/2007 | Deem et al. |
| 2007/0055180 A1 | 3/2007 | Deem et al. |
| 2007/0055181 A1 | 3/2007 | Deem et al. |
| 2007/0073367 A1 | 3/2007 | Jones et al. |
| 2007/0078502 A1 | 4/2007 | Weber et al. |
| 2007/0100398 A1 | 5/2007 | Sloan |
| 2007/0106342 A1 | 5/2007 | Schumann |
| 2007/0129714 A1 | 6/2007 | Elkins et al. |
| 2007/0135876 A1 | 6/2007 | Weber |
| 2007/0141265 A1 | 6/2007 | Thomson |
| 2007/0179482 A1 | 8/2007 | Anderson |
| 2007/0198071 A1 | 8/2007 | Ting et al. |
| 2007/0219540 A1 | 9/2007 | Masotti et al. |
| 2007/0239075 A1 | 10/2007 | Rosenberg et al. |
| 2007/0239150 A1 | 10/2007 | Zvuloni et al. |
| 2007/0249519 A1 | 10/2007 | Guha et al. |
| 2007/0255187 A1 | 11/2007 | Branch |
| 2007/0255274 A1 | 11/2007 | Stern et al. |
| 2007/0255362 A1 | 11/2007 | Levinson et al. |
| 2007/0265585 A1 | 11/2007 | Joshi et al. |
| 2007/0265614 A1 | 11/2007 | Stern et al. |
| 2007/0270925 A1 | 11/2007 | Levinson |
| 2007/0282249 A1 | 12/2007 | Quisenberry et al. |
| 2007/0282318 A1 | 12/2007 | Spooner et al. |
| 2008/0014627 A1 | 1/2008 | Merchant et al. |
| 2008/0046047 A1 | 2/2008 | Jacobs |
| 2008/0058784 A1 | 3/2008 | Manstein et al. |
| 2008/0077201 A1 | 3/2008 | Levinson et al. |
| 2008/0077202 A1 | 3/2008 | Levinson |
| 2008/0077211 A1 | 3/2008 | Levinson et al. |
| 2008/0097207 A1* | 4/2008 | Cai .................. A61B 8/08 600/442 |
| 2008/0139901 A1 | 6/2008 | Altshuler et al. |
| 2008/0140061 A1 | 6/2008 | Toubia et al. |
| 2008/0140371 A1 | 6/2008 | Warner |
| 2008/0161892 A1 | 7/2008 | Mercuro et al. |
| 2008/0183164 A1 | 7/2008 | Elkins et al. |
| 2008/0188915 A1 | 8/2008 | Mills et al. |
| 2008/0248554 A1 | 10/2008 | Merchant et al. |
| 2008/0269851 A1 | 10/2008 | Deem et al. |
| 2008/0287839 A1 | 11/2008 | Rosen et al. |
| 2008/0300529 A1 | 12/2008 | Reinstein |
| 2008/0312651 A1 | 12/2008 | Pope et al. |
| 2009/0012434 A1 | 1/2009 | Anderson |
| 2009/0018623 A1 | 1/2009 | Levinson et al. |
| 2009/0018624 A1 | 1/2009 | Levinson et al. |
| 2009/0018625 A1 | 1/2009 | Levinson et al. |
| 2009/0018626 A1 | 1/2009 | Levinson et al. |
| 2009/0018627 A1 | 1/2009 | Levinson et al. |
| 2009/0024023 A1 | 1/2009 | Welches et al. |
| 2009/0076488 A1 | 3/2009 | Welches et al. |
| 2009/0112134 A1 | 4/2009 | Avni |
| 2009/0118722 A1 | 5/2009 | Ebbers et al. |
| 2009/0149929 A1 | 6/2009 | Levinson et al. |
| 2009/0149930 A1 | 6/2009 | Schenck |
| 2009/0171253 A1 | 7/2009 | Davenport |
| 2009/0171334 A1 | 7/2009 | Elkins et al. |
| 2009/0209886 A1* | 8/2009 | Tudico .................. A61H 7/008 601/6 |
| 2009/0221938 A1 | 9/2009 | Rosenberg et al. |
| 2009/0276018 A1 | 11/2009 | Brader |
| 2009/0281464 A1 | 11/2009 | Cioanta et al. |
| 2009/0299234 A1* | 12/2009 | Cho .................. A61H 9/0057 601/2 |
| 2009/0306749 A1 | 12/2009 | Mulindwa |
| 2009/0312676 A1 | 12/2009 | Rousso et al. |
| 2009/0312693 A1 | 12/2009 | Thapliyal et al. |
| 2009/0326621 A1 | 12/2009 | El-Galley |
| 2010/0015190 A1 | 1/2010 | Hassler |
| 2010/0028969 A1 | 2/2010 | Mueller et al. |
| 2010/0030306 A1 | 2/2010 | Edelman et al. |
| 2010/0036295 A1 | 2/2010 | Altshuler et al. |
| 2010/0042087 A1 | 2/2010 | Goldboss et al. |
| 2010/0049178 A1 | 2/2010 | Deem et al. |
| 2010/0081971 A1 | 4/2010 | Allison |
| 2010/0087806 A1 | 4/2010 | Da Silva et al. |
| 2010/0152824 A1 | 6/2010 | Allison |
| 2010/0168726 A1 | 7/2010 | Brookman |
| 2010/0179531 A1 | 7/2010 | Nebrigic et al. |
| 2010/0198064 A1 | 8/2010 | Perl et al. |
| 2010/0217349 A1 | 8/2010 | Fahey et al. |
| 2010/0268220 A1 | 10/2010 | Johnson et al. |
| 2010/0280582 A1* | 11/2010 | Baker .................. A61F 7/007 607/113 |
| 2011/0009860 A1 | 1/2011 | Chornenky et al. |
| 2011/0040235 A1 | 2/2011 | Castel |
| 2011/0040299 A1 | 2/2011 | Kim et al. |
| 2011/0046523 A1 | 2/2011 | Altshuler et al. |
| 2011/0060323 A1 | 3/2011 | Baust et al. |
| 2011/0066083 A1 | 3/2011 | Tosaya et al. |
| 2011/0066216 A1 | 3/2011 | Ting et al. |
| 2011/0077557 A1 | 3/2011 | Wing et al. |
| 2011/0077723 A1 | 3/2011 | Parish et al. |
| 2011/0112405 A1 | 5/2011 | Barthe et al. |
| 2011/0112520 A1 | 5/2011 | Kreindel |
| 2011/0144631 A1 | 6/2011 | Elkins et al. |
| 2011/0152849 A1 | 6/2011 | Baust et al. |
| 2011/0172651 A1 | 7/2011 | Altshuler et al. |
| 2011/0189129 A1 | 8/2011 | Qiu et al. |
| 2011/0196395 A1 | 8/2011 | Maschke |
| 2011/0196438 A1 | 8/2011 | Mnozil et al. |
| 2011/0202048 A1 | 8/2011 | Nebrigic et al. |
| 2011/0238050 A1 | 9/2011 | Allison et al. |
| 2011/0238051 A1 | 9/2011 | Levinson et al. |
| 2011/0257642 A1 | 10/2011 | Griggs, III |
| 2011/0300079 A1 | 12/2011 | Martens et al. |
| 2011/0301585 A1 | 12/2011 | Goulko |
| 2011/0313411 A1 | 12/2011 | Anderson et al. |
| 2011/0313412 A1 | 12/2011 | Kim et al. |
| 2012/0010609 A1 | 1/2012 | Deem et al. |
| 2012/0016239 A1 | 1/2012 | Barthe et al. |
| 2012/0022518 A1 | 1/2012 | Levinson |
| 2012/0022622 A1 | 1/2012 | Johnson et al. |
| 2012/0035475 A1 | 2/2012 | Barthe et al. |
| 2012/0035476 A1 | 2/2012 | Barthe et al. |
| 2012/0046547 A1 | 2/2012 | Barthe et al. |
| 2012/0053458 A1 | 3/2012 | Barthe et al. |
| 2012/0065629 A1 | 3/2012 | Elkins et al. |
| 2012/0083862 A1 | 4/2012 | Altshuler et al. |
| 2012/0101549 A1 | 4/2012 | Schumann |
| 2012/0109041 A1 | 5/2012 | Munz |
| 2012/0158100 A1 | 6/2012 | Schomacker |

(56) References Cited

U.S. PATENT DOCUMENTS

| | | |
|---|---|---|
| 2012/0209363 A1 | 8/2012 | Williams, III et al. |
| 2012/0233736 A1 | 9/2012 | Tepper et al. |
| 2012/0239123 A1* | 9/2012 | Weber .................. A61F 7/02 607/104 |
| 2012/0253416 A1 | 10/2012 | Erez et al. |
| 2012/0259322 A1 | 10/2012 | Fourkas et al. |
| 2012/0277674 A1 | 11/2012 | Clark, III et al. |
| 2012/0310232 A1 | 12/2012 | Erez |
| 2013/0018236 A1 | 1/2013 | Altshuler et al. |
| 2013/0019374 A1 | 1/2013 | Schwartz |
| 2013/0066309 A1 | 3/2013 | Levinson |
| 2013/0073017 A1 | 3/2013 | Liu et al. |
| 2013/0079684 A1 | 3/2013 | Rosen et al. |
| 2013/0116758 A1 | 5/2013 | Levinson et al. |
| 2013/0116759 A1 | 5/2013 | Levinson et al. |
| 2013/0150844 A1 | 6/2013 | Deem et al. |
| 2013/0158440 A1 | 6/2013 | Allison |
| 2013/0158636 A1 | 6/2013 | Ting et al. |
| 2013/0166003 A1 | 6/2013 | Johnson et al. |
| 2013/0190744 A1 | 7/2013 | Avram et al. |
| 2013/0238062 A1 | 9/2013 | Ron et al. |
| 2013/0245507 A1 | 9/2013 | Khorassani |
| 2013/0253384 A1 | 9/2013 | Anderson et al. |
| 2013/0253493 A1 | 9/2013 | Anderson et al. |
| 2013/0253494 A1 | 9/2013 | Anderson et al. |
| 2013/0253495 A1 | 9/2013 | Anderson et al. |
| 2013/0253496 A1 | 9/2013 | Anderson et al. |
| 2013/0303904 A1 | 11/2013 | Barthe et al. |
| 2013/0303905 A1 | 11/2013 | Barthe et al. |
| 2013/0331914 A1 | 12/2013 | Lee et al. |
| 2014/0005759 A1 | 1/2014 | Fahey et al. |
| 2014/0005760 A1 | 1/2014 | Levinson et al. |
| 2014/0067025 A1 | 3/2014 | Levinson et al. |
| 2014/0142469 A1 | 5/2014 | Britva et al. |
| 2014/0200487 A1 | 7/2014 | Ramdas et al. |
| 2014/0200488 A1 | 7/2014 | Seo et al. |
| 2014/0222121 A1 | 8/2014 | Spence et al. |
| 2014/0277219 A1 | 9/2014 | Nanda |
| 2014/0277302 A1 | 9/2014 | Weber et al. |
| 2014/0277303 A1 | 9/2014 | Biser et al. |
| 2014/0303697 A1 | 10/2014 | Anderson et al. |
| 2015/0209174 A1 | 7/2015 | Abreu |
| 2015/0216719 A1 | 8/2015 | DeBenedictis et al. |
| 2015/0216720 A1 | 8/2015 | DeBenedictis et al. |
| 2015/0216816 A1 | 8/2015 | O'Neil et al. |
| 2015/0223975 A1 | 8/2015 | Anderson et al. |
| 2015/0283022 A1 | 10/2015 | Lee et al. |
| 2015/0328077 A1 | 11/2015 | Levinson |
| 2015/0335468 A1 | 11/2015 | Rose et al. |
| 2015/0342780 A1 | 12/2015 | Levinson et al. |
| 2016/0051308 A1 | 2/2016 | Pennybacker et al. |
| 2016/0051401 A1 | 2/2016 | Yee et al. |
| 2016/0135985 A1 | 5/2016 | Anderson |
| 2016/0324684 A1 | 11/2016 | Levinson et al. |
| 2017/0007309 A1 | 1/2017 | DeBenedictis et al. |
| 2017/0079833 A1 | 3/2017 | Frangineas, Jr. et al. |
| 2017/0105869 A1 | 4/2017 | Frangineas, Jr. et al. |
| 2017/0165105 A1 | 6/2017 | Anderson et al. |
| 2017/0196731 A1 | 7/2017 | DeBenedictis et al. |
| 2017/0239079 A1 | 8/2017 | Root et al. |
| 2017/0325992 A1 | 11/2017 | DeBenedictis et al. |
| 2017/0325993 A1 | 11/2017 | Jimenez Lozano et al. |
| 2017/0326042 A1 | 11/2017 | Zeng et al. |
| 2017/0326346 A1 | 11/2017 | Jimenez Lozano et al. |
| 2018/0185081 A1 | 7/2018 | O'neil et al. |
| 2018/0185189 A1 | 7/2018 | Weber et al. |

FOREIGN PATENT DOCUMENTS

| | | |
|---|---|---|
| CH | 333982 A | 11/1958 |
| CN | 86200604 U | 10/1987 |
| CN | 2514795 Y | 10/2002 |
| CN | 2514811 Y | 10/2002 |
| CN | 1511503 A | 7/2004 |
| CN | 1741777 A | 3/2006 |
| CN | 1817990 A | 8/2006 |
| CN | 2843367 Y | 12/2006 |
| CN | 2850584 Y | 12/2006 |
| CN | 2850585 Y | 12/2006 |
| CN | 200970265 Y | 11/2007 |
| CN | 101259329 A | 9/2008 |
| DE | 532976 C | 9/1931 |
| DE | 2851602 A1 | 6/1980 |
| DE | 4213584 A1 | 11/1992 |
| DE | 4224595 A1 | 1/1994 |
| DE | 4238291 A1 | 5/1994 |
| DE | 4445627 A1 | 6/1996 |
| DE | 19800416 A1 | 7/1999 |
| EP | 263069 A2 | 4/1988 |
| EP | 0397043 A1 | 11/1990 |
| EP | 0406244 A1 | 1/1991 |
| EP | 560309 A1 | 9/1993 |
| EP | 0598824 A1 | 6/1994 |
| EP | 1030611 A1 | 8/2000 |
| EP | 1201266 A1 | 5/2002 |
| EP | 1568395 A1 | 8/2005 |
| EP | 2260801 A2 | 12/2010 |
| EP | 2289598 A1 | 3/2011 |
| EP | 2527005 A1 | 11/2012 |
| FR | 854937 A | 4/1940 |
| FR | 2744358 A1 | 8/1997 |
| FR | 2745935 A1 | 9/1997 |
| FR | 2767476 A1 | 2/1999 |
| FR | 2776920 A1 | 10/1999 |
| FR | 2789893 A1 | 8/2000 |
| FR | 2805989 A1 | 9/2001 |
| GB | 387960 A | 2/1933 |
| GB | 2120944 A | 12/1983 |
| GB | 2202447 A | 9/1988 |
| GB | 2248183 A | 4/1992 |
| GB | 2263872 A | 8/1993 |
| GB | 2286660 A | 8/1995 |
| GB | 2323659 A | 9/1998 |
| JP | 58187454 A | 11/1983 |
| JP | S6094113 U | 6/1985 |
| JP | 62082977 A | 4/1987 |
| JP | 63076895 A | 4/1988 |
| JP | 01223961 A | 9/1989 |
| JP | 03051964 A | 3/1991 |
| JP | 03259975 A | 11/1991 |
| JP | 04093597 A | 3/1992 |
| JP | 06261933 A | 9/1994 |
| JP | 07194666 A | 8/1995 |
| JP | 07268274 A | 10/1995 |
| JP | 09164163 A | 6/1997 |
| JP | 10216169 A | 8/1998 |
| JP | 10223961 A | 8/1998 |
| JP | 2000503154 A | 3/2000 |
| JP | 3065657 B2 | 7/2000 |
| JP | 2001046416 A | 2/2001 |
| JP | 2002125993 A | 5/2002 |
| JP | 2002224051 A | 8/2002 |
| JP | 2002282295 A | 10/2002 |
| JP | 2002290397 A | 10/2002 |
| JP | 2002543668 A | 12/2002 |
| JP | 2003190201 A | 7/2003 |
| JP | 2004013600 A | 1/2004 |
| JP | 2004073812 A | 3/2004 |
| JP | 2004159666 A | 6/2004 |
| JP | 2005039790 A | 2/2005 |
| JP | 2005065984 A | 3/2005 |
| JP | 2005110755 A | 4/2005 |
| JP | 2005509977 A | 4/2005 |
| JP | 3655820 B2 | 6/2005 |
| JP | 2005520608 A | 7/2005 |
| JP | 2005237908 A | 9/2005 |
| JP | 2005323716 A | 11/2005 |
| JP | 2006026001 A | 2/2006 |
| JP | 2006130055 A | 5/2006 |
| JP | 2006520949 A | 9/2006 |
| JP | 2007270459 A | 10/2007 |
| JP | 2008532591 A | 8/2008 |
| JP | 2009515232 A | 4/2009 |

(56) References Cited

FOREIGN PATENT DOCUMENTS

| | | |
|---|---|---|
| JP | 2009189757 A | 8/2009 |
| KR | 200173222 Y1 | 12/1999 |
| KR | 1020040094508 A | 11/2004 |
| KR | 20090000258 U | 1/2009 |
| KR | 1020130043299 A | 4/2013 |
| KR | 1020140038165 A | 3/2014 |
| RU | 2036667 C1 | 6/1995 |
| SU | 532976 A1 | 11/1978 |
| TW | 0476644 B | 2/2002 |
| WO | 8503216 A1 | 8/1985 |
| WO | 9114417 A1 | 10/1991 |
| WO | 9404116 A1 | 3/1994 |
| WO | 9623447 A1 | 8/1996 |
| WO | 9626693 A1 | 9/1996 |
| WO | 9636293 A1 | 11/1996 |
| WO | 9637158 A1 | 11/1996 |
| WO | 9704832 A1 | 2/1997 |
| WO | 9705828 A1 | 2/1997 |
| WO | 9722262 A2 | 6/1997 |
| WO | 9724088 A1 | 7/1997 |
| WO | 9725798 A1 | 7/1997 |
| WO | 9748440 A1 | 12/1997 |
| WO | 9829134 A2 | 7/1998 |
| WO | 9831321 A1 | 7/1998 |
| WO | 9841156 A1 | 9/1998 |
| WO | 9841157 A1 | 9/1998 |
| WO | 9909928 A1 | 3/1999 |
| WO | 9916502 A1 | 4/1999 |
| WO | 9938469 A1 | 8/1999 |
| WO | 9949937 A1 | 10/1999 |
| WO | 0044346 A1 | 8/2000 |
| WO | 0044349 A1 | 8/2000 |
| WO | 0065770 A1 | 11/2000 |
| WO | 0067685 A1 | 11/2000 |
| WO | 0100269 A1 | 1/2001 |
| WO | 0113989 A1 | 3/2001 |
| WO | 0114012 A1 | 3/2001 |
| WO | 0134048 A1 | 5/2001 |
| WO | 0205736 A1 | 1/2002 |
| WO | 02102921 A1 | 12/2002 |
| WO | 03007859 A1 | 1/2003 |
| WO | 03078596 A2 | 9/2003 |
| WO | 03079916 A1 | 10/2003 |
| WO | 2004000098 A2 | 12/2003 |
| WO | 2004080279 A2 | 9/2004 |
| WO | 2004090939 A2 | 10/2004 |
| WO | 2005033957 A1 | 4/2005 |
| WO | 2005046540 A1 | 5/2005 |
| WO | 2005060354 A2 | 7/2005 |
| WO | 2005096979 A1 | 10/2005 |
| WO | 2005112815 A1 | 12/2005 |
| WO | 2006066226 A1 | 6/2006 |
| WO | 2006094348 A1 | 9/2006 |
| WO | 2006106836 A1 | 10/2006 |
| WO | 2006116603 A2 | 11/2006 |
| WO | 2006127467 A2 | 11/2006 |
| WO | 2007012083 A2 | 1/2007 |
| WO | 2007028975 A1 | 3/2007 |
| WO | 2007041642 A2 | 4/2007 |
| WO | 2007101039 A1 | 9/2007 |
| WO | 2007127924 A2 | 11/2007 |
| WO | 2007145421 A1 | 12/2007 |
| WO | 2007145422 A1 | 12/2007 |
| WO | 2008006018 A2 | 1/2008 |
| WO | 2008039556 A1 | 4/2008 |
| WO | 2008039557 A1 | 4/2008 |
| WO | 2008055243 A2 | 5/2008 |
| WO | 2008143678 A1 | 11/2008 |
| WO | 2009011708 A1 | 1/2009 |
| WO | 2009026471 A1 | 2/2009 |
| WO | 2010077841 A1 | 7/2010 |
| WO | 2010127315 A2 | 11/2010 |
| WO | 2012012296 A1 | 1/2012 |
| WO | 2012103242 A1 | 8/2012 |
| WO | 2013013059 A1 | 1/2013 |
| WO | 2013075006 A1 | 5/2013 |
| WO | 2013075016 A1 | 5/2013 |
| WO | 2013190337 A1 | 12/2013 |
| WO | 2014151872 A3 | 9/2014 |
| WO | 2014191263 A1 | 12/2014 |
| WO | 2015117001 A1 | 8/2015 |
| WO | 2015117005 A1 | 8/2015 |
| WO | 2015117026 A2 | 8/2015 |
| WO | 2015117032 A1 | 8/2015 |
| WO | 2015117036 A2 | 8/2015 |
| WO | 2016028796 A1 | 2/2016 |
| WO | 2016048721 A1 | 3/2016 |

OTHER PUBLICATIONS

Aguilar et al., "Modeling Cryogenic Spray Temperature and Evaporation Rate Based on Single-Droplet Analysis," Eighth International Conference on Liquid Atomization and Spray Systems, Pasadena, CA, USA, Jul. 2000, 7 pages.

Al-Sakere, B. et al. "Tumor Ablation with Irreversible Electroporation," PLoS One, Issue 11, Nov. 2007, 8 pages.

Alster, T. et al., "Cellulite Treatment Using a Novel Combination Radiofrequency, Infrared Light, and Mechanical Tissue Manipulation Device," Journal of Cosmetic and Laser Therapy, vol. 7, 2005, pp. 81-85.

Ardevol, A. et al., "Cooling Rates of Tissue Samples During Freezing with Liquid Nitrogen," Journal of Biochemical and Biophysical Methods, vol. 27, 1993, pp. 77-86.

Arena, C. B. et al., "High-Frequency Irreversible Electroporation (H-FIRE) for Non-Thermal Ablation Without Muscle Contraction," BioMedical Engineering OnLine 2011, 10:102, Nov. 21, 2011, 21 pgs.

Becker, S. M. et al. "Local Temperature Rises Influence In Vivo Electroporation Pore Development: A Numerical Stratum Corneum Lipid Phase Transition Model," Journal of Biomechanical Engineering, vol. 129, Oct. 2007, pp. 712-721.

Bohm, T. et al., "Saline-Enhanced Radiofrequency Ablation of Breast Tissue: an in Vitro Feasibility Study," Investigative Radiology, vol. 35 (3), 2000, pp. 149-157.

Bondei, E. et al., "Disorders of Subcutaneous Tissue (Cold Panniculitis)," Dermatology in General Medicine, Fourth Edition, vol. 1, Chapter 108, 1993, Section 16, pp. 1333-1334.

Burge, S.M. et al., "Hair Follicle Destruction and Regeneration in Guinea Pig Skin after Cutaneous Freeze Injury," Cryobiology, 27(2), 1990, pp. 153-163.

Coban, Y. K. et al., "Ischemia-Reperfusion Injury of Adipofascial Tissue: An Experimental Study Evaluating Early Histologic and Biochemical Alterations in Rats," Mediators of Inflammation, 2005, 5, pp. 304-308.

Del Pino, M. E. et al. "Effect of Controlled Volumetric Tissue Heating with Radiofrequency on Cellulite and the Subcutaneous Tissue of the Buttocks and Thighs," Journal of Drugs in Dermatology, vol. 5, Issue 8, Sep. 2006, pp. 714-722.

Donski, P. K. et al., "The Effects of Cooling no Experimental Free Flap Survival," British Journal of Plastic Surgery, vol. 33, 1980, pp. 353-360.

Duck, F. A., Physical Properties of Tissue, Academic Press Ltd., chapters 4 & 5, 1990, pp. 73-165.

Duncan, W. C. et al., "Cold Panniculitis," Archives of Dermatology, vol. 94, Issue 6, Dec. 1966, pp. 722-724.

Epstein, E. H. et al., "Popsicle Panniculitis," The New England Journal of Medicine, 282(17), Apr. 23, 1970, pp. 966-967.

Fournier, L. et al. "Lattice Model for the Kinetics of Rupture of Fluid Bilayer Membranes," Physical Review, vol. 67, 2003, pp. 051908-1-051908-11.

Gabriel, S. et al., "The Dielectric Properties of Biological Tissues: II. Measurements in the Frequency Range 10 Hz to 20 GHz," Physics in Medicine and Biology, vol. 41, 1996, pp. 2251-2269.

Gage, A. "Current Progress in Cryosurgery," Cryobiology 25, 1988, pp. 483-486.

Gatto, H. "Effects of Thermal Shocks on Interleukin-1 Levels and Heat Shock Protein 72 (HSP72) Expression in Normal Human

(56) References Cited

OTHER PUBLICATIONS

Keratinocytes," PubMed, Archives of Dermatological Research, vol. 284, Issue 7, 1992: pp. 414-417 [Abstract].
Hale, H. B. et al., "Influence of Chronic Heat Exposure and Prolonged Food Deprivation on Excretion of Magnesium, Phosphorus, Calcium, Hydrogen Ion & Ketones," Aerospace Medicine, vol. 39—No. 9, Sep. 1968, pp. 919-926.
Heller Page, E. et al., "Temperature-dependent skin disorders," Journal of the American Academy of Dermatology, vol. 18, No. 5, Pt 1, May 1988, pp. 1003-1019.
Hemmingsson, A. et al. "Attenuation in Human Muscle and Fat Tissue in Vivo and in Vitro," Acra Radiologica Diagnosis, vol. 23, No. 2, 1982, pp. 149-151.
Henry, F. et al., "Les Dermatoses Hivernales," Rev Med Liege, 54:11, 1999, pp. 864-866. [Abstract Attached].
Hernan, P. et al., "Study for the evaluation of the efficacy of Lipocryolysis (EEEL)", Nov. 30, 2011.
Hernan, R. P., "A Study to Evaluate the Action of Lipocryolysis", 33(3) CryoLellers, 2012, pp. 176-180.
Holland, DB. et al. "Cold shock induces the synthesis of stress proteins in human keratinocytes," PubMed Journal of Investigative Dermatology; 101(2): Aug. 1993, pp. 196-199.
Holman, W. L. et al., "Variation in Cryolesion Penetration Due to Probe Size and Tissue Thermal Conductivity," The Annals of Thoracic Surgery, vol. 53, 1992, pp. 123-126.
Hong, J.S. et al., "Patterns of Ice Formation in Normal and Malignant Breast Tissue," Cryobiology 31, 1994, pp. 109-120.
Huang et al. "Comparative Proteomic Profiling of Murine Skin," Journal of Investigative Dermatology, vol. 121(1), Jul. 2003, pp. 51-64.
Isambert, H. "Understanding the Electroporation of Cells and Artificial Bilayer Membranes," Physical Review Letters, vol. 80, No. 15, 1998, pp. 3404-3707.
Jalian, H. R. et al., "Cryolipolysis: A Historical Perspective and Current Clinical Practice", 32(1) Semin. Cutan. Med. Surg., 2013, pp. 31-34.
Kellum, R. E. et al., "Sclerema Neonatorum: Report of Case and Analysis of Subcutaneous and Epidermal-Dermal Lipids by Chromatographic Methods," Archives of Dermatology, vol. 97, Apr. 1968, pp. 372-380.
Koska, J. et al., "Endocrine Regulation of Subcutaneous Fat Metabolism During Cold Exposure in Humans," Annals of the New York Academy of Sciences, vol. 967, 2002, pp. 500-505.
Kundu, S. K. et al., "Breath Acetone Analyzer: Diagnostic Tool to Monitor Dietary Fat Loss," Clinical Chemistry, vol. 39, Issue (1), 1993, pp. 87-92.
Kundu, S. K. et al., "Novel Solid-Phase Assay of Ketone Bodies in Urine," Clinical Chemistry, vol. 37, Issue (9), 1991, pp. 1565-1569.
Kuroda, S. et al. "Thermal Distribution of Radio-Frequency Inductive Hyperthermia Using an Inductive Aperture-Type Applicator: Evaluation of the Effect of Tumor Size and Depth", Medical and Biological Engineering and Computing, vol. 37, 1999, pp. 285-290.
Laugier, P. et al., "In Vivo Results with a New Device for Ultrasonic Monitoring of Pig Skin Cryosurgery: The Echographic Cryprobe," The Society for Investigative Dermatology, Inc., vol. 111, No. 2, Aug. 1998, pp. 314-319.
Levchenko et al., "Effect of Dehydration on Lipid Metabolism" Ukrainskii Biokhimicheskii Zhurnal, vol. 50, Issue 1, 1978, pp. 95-97.
Lidagoster, MD et al., "Comparison of Autologous Fat Transfer in Fresh, Refrigerated, and Frozen Specimens: An Animal Model," Annals of Plastic Surgery, vol. 44, No. 5, May 2000, pp. 512-515.
Liu, A. Y.-C. et al., "Transient Cold Shock Induces the Heat Shock Response upon Recovery at 37 C in Human Cells," Journal of Biological Chemistry 269(20), May 20, 1994, pp. 14768-14775.
L'Vova, S.P. "Lipid Levels and Lipid Peroxidation in Frog Tissues During Hypothermia and Hibernation" Ukrainskii Biokhimicheskii Zhurnal, vol. 62, Issue 1, 1990, pp. 65-70.
Maize, J.C. "Panniculitis," Cutaneous Pathology, Chapter 13, 1998, 327-344.

Malcolm, G. T. et al., "Fatty Acid Composition of Adipose Tissue in Humans: Differences between Subcutaneous Sites," The American Journal of Clinical Nutrition, vol. 50, 1989, pp. 288-291.
Manstein, D. et al. "A Novel Cryotherapy Method of Non-invasive, Selective Lipolysis," LasersSurg.Med 40:S20, 2008, p. 104.
Manstein, D. et al. "Selective Cryolysis: A Novel Method of Non-Invasive Fat Removal," Lasers in Surgery and Medicine: The Official Journal of the ASLMS, vol. 40, No. 9, Nov. 2008, pp. 595-604.
Mayoral, "Case Reports: Skin Tightening with a Combined Unipolar and Bipolar Radiofrequency Device," Journal of Drugs in Dermatology, 2007, pp. 212-215.
Mazur, P. "Cryobiology: the Freezing of Biological Systems," Science, 68, 1970, pp. 939-949.
Merrill, T. "A Chill to the Heart: A System to Deliver Local Hypothermia Could One Day Improve the Lives of Heart-Attack Patients," Mechanical Engineering Magazine, Oct. 2010, 10 pages.
Miklavcic, D. et al. "Electroporation-Based Technologies and Treatments," The Journal of Membrane Biology (2010) 236:1-2, 2 pgs.
Moschella, S. L. et al., "Diseases of the Subcutaneous Tissue," in Dermatology, Second Edition, vol. 2, 1985 Chapter 19, Section II (W.B. Saunders Company, 1980) pp. 1169-1181.
Murphy, J. V. et al., "Frostbite: Pathogenesis and Treatment" The Journal of Trauma: Injury, Infection, and Critical Care, vol. 48, No. 1, Jan. 2000, pp. 171-178.
Nagao, T. et al., " Dietary Diacylglycerol Suppresses Accumulation of Body Fat Compared to Triacylglycerol in Men a Double-Blind Controlled Trial," The Journal of Nutrition, vol. 130, Issue (4), 2000, pp. 792-797.
Nagle, W. A. et al. "Cultured Chinese Hamster Cells Undergo Apoptosis After Exposure to Cold but Nonfreezing Temperatures," Cryobiology 27, 1990, pp. 439-451.
Nagore, E. et al., "Lipoatrophia Semicircularis—a Traumatic Panniculitis: Report of Seven Cases and Review of the Literature," Journal of the American Academy of Dermatology, vol. 39, Nov. 1998, pp. 879-881.
Nanda, G.S. et al., "Studies on electroporation of thermally and chemically treated human erythrocytes," Bioelectrochemistry and Bioenergetics, 34, 1994, pp. 129-134, 6 pgs.
Narins, D.J. et al. "Non-Surgical Radiofrequency Facelift", The Journal of Drugs in Dermatology, vol. 2, Issue 5, 2003, pp. 495-500.
Nielsen, B. "Thermoregulation in Rest and Exercise," Acta Physiologica Scandinavica Supplementum, vol. 323 (Copenhagen 1969), pp. 7-74.
Nishikawa, H. et al. "Ultrastructural Changes and Lipid Peroxidation in Rat Adipomusculocutaneous Flap Isotransplants after Normothermic Storage and Reperfusion," Transplantation, vol. 54, No. 5,1992, pp. 795-801.
Nurnberger, F. "So-Called Cellulite: An Invented Disease," Journal of Dermatologic Surgery and Oncology, Mar. 1978, pp. 221-229.
Pease, G. R. et al., "An Integrated Probe for Magnetic Resonance Imaging Monitored Skin Cryosurgery," Journal of Biomedical Engineering, vol. 117, Feb. 1995, pp. 59-63.
Pech, P. et al., "Attenuation Values, Volume Changes and Artifacts in Tissue Due to Freezing," Acta Radiologica ,vol. 28, Issue 6, 1987, pp. 779-782.
Peterson, L. J. et al., "Bilateral Fat Necrosis of the Scrotum," Journal of Urology, vol. 116, 1976, pp. 825-826.
Phinney, S. D. et al., "Human Subcutaneous Adipose Tissue Shows Site-Specific Differences in Fatty Acid Composition," The American Journal of Clinical Nutrition, vol. 60, 1994, pp. 725-729.
Pierard, G.E. et al., "Cellulite: From Standing Fat Herniation to Hypodermal Stretch Marks," The American Journal of Dermatology, vol. 22, Issue 1, 2000, pp. 34-37, [Abstract].
Pope, K. et al. "Selective Fibrous Septae Heating: An Additional Mechanism of Action for Capacitively Coupled Monopolar Radiofrequency" Thermage, Inc. Article, Feb. 2005, 6pgs.
Quinn, P. J. "A Lipid-Phase Separation Model of Low-Temperature Damage to Biological Membranes," Cryobiology, 22, 1985, 128-146.
Rabi, T. et al., "Metabolic Adaptations in Brown Adipose Tissue of the Hamster in Extreme Ambient Temperatures," American Journal of Physiology, vol. 231, Issue 1, Jul. 1976, pp. 153-160.

(56) References Cited

OTHER PUBLICATIONS

Renold, A.E. et al. "Adipose Tissue" in Handbook of Physiology, Chapter 15, (Washington, D.C., 1965) pp. 169-176.
Rossi, A. B. R. et al. "Cellulite: a Review," European Academy of Dermatology and Venercology, 2000, pp. 251-262, 12 pgs.
Rubinsky, B. "Principles of Low Temperature Cell Preservation," Heart Failure Reviews, vol. 8, 2003, pp. 277-284.
Rubinsky, B. et al., "Cryosurgery: Advances in the Application of low Temperatures to Medicine," International Journal of Refrigeration, vol. 14, Jul. 1991, pp. 190-199.
Saleh, K.Y. et al., "Two-Dimensional Ultrasound Phased Array Design for Tissue Ablation for Treatment of Benign Prostatic Hyperplasia," International Journal of Hyperthermia, vol. 20, No. 1, Feb. 2004, pp. 7-31.
Schoning, P. et al., "Experimental Frostbite: Freezing Times, Rewarming Times, and Lowest Temperatures of Pig Skin Exposed to Chilled Air," Cryobiology 27, 1990, pp. 189-193.
Shephard, R. J. "Adaptation to Exercise in the Cold," Sports Medicine, vol. 2, 1985, pp. 59-71.
Sigma-Aldrich "Poly(ethylene glycol) and Poly(ethylene oxide)," http://www.sigmaaldrich.com/materials-science/materialscience-;products.htmi?TablePage=2020411 0, accessed Oct. 19, 2012.
Smalls, L. K. et al. "Quantitative Model of Cellulite: Three Dimensional Skin Surface Topography, Biophysical Characterization, and Relationship to Human Perception," International Journal of Cosmetic Science, vol. 27, Issue 5, Oct. 2005, 17 pgs.
Thermage, News Release, "Study Published in Facial Plastic Surgery Journal Finds Selective Heating of Fibrous Septae Key to Success and Safety of Thermage ThermaCool System," Jun. 20, 2005, 2 pages.
Vallerand et al. "Cold Stress Increases Lipolysis, FFA Ra and TG/FFA Cycling in Humans," Aviation, Space, and Environmental Medicine 70(1), 1999, pp. 42-50.
Wang, X. et al., "Cryopreservation of Cell/Hydrogel Constructs Based on a new Cell-Assembling Technique," Sep. 5, 2009, 40 pages.
Wharton, D. A. et al., "Cold Acclimation and Cryoprotectants in a Freeze-Tolerant Antarctic Nematode, Panagrolaimus Davidi,", Journal of Comparative Physiology, vol. 170, No. 4, Mar. 2000, 2 pages.
Winkler, C. et al., "Gene Transfer in Laboratory Fish: Model Organisms for the Analysis of Gene Function," in Transgenic Animals, Generation and Use (The Netherlands 1997), pp. 387-395.
Young, H. E. et al. "Isolation of Embryonic Chick Myosatellite and Pluripotent Stem Cells" The Journal of Tissue Culture Methods, vol. 14, Issue 2, 1992, pp. 85-92.
Zelickson, B. et al., "Cryolipolysis for Noninvasive Fat Cell Destruction: Initial Results from a Pig Model", 35 Dermatol. Sug., 2009, pp. 1-9.
Zouboulis, C. C. et al., "Current Developments and Uses of Cryosurgery in the Treatment of Keloids and Hypertrophic Scars," Wound Repair and Regeneration, vol. 10, No. 2, 2002, pp. 98-102.

\* cited by examiner

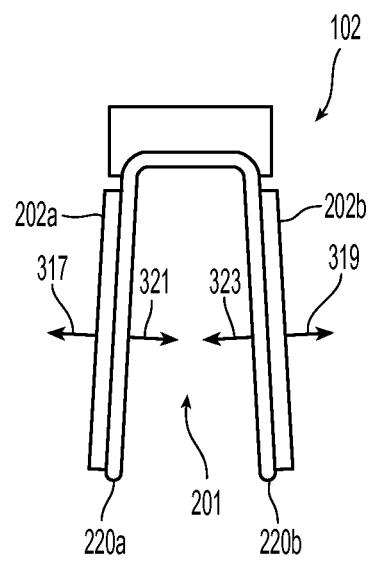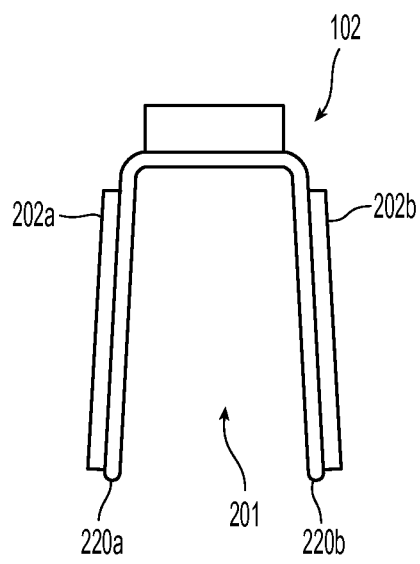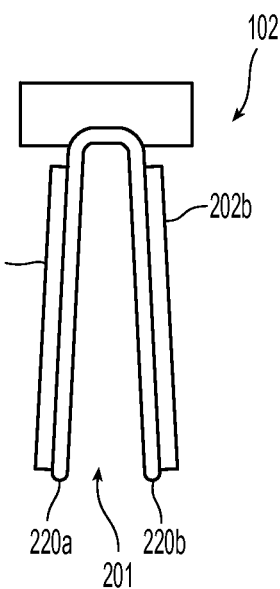
Fig. 7　　　　　Fig. 8　　　　　Fig. 9
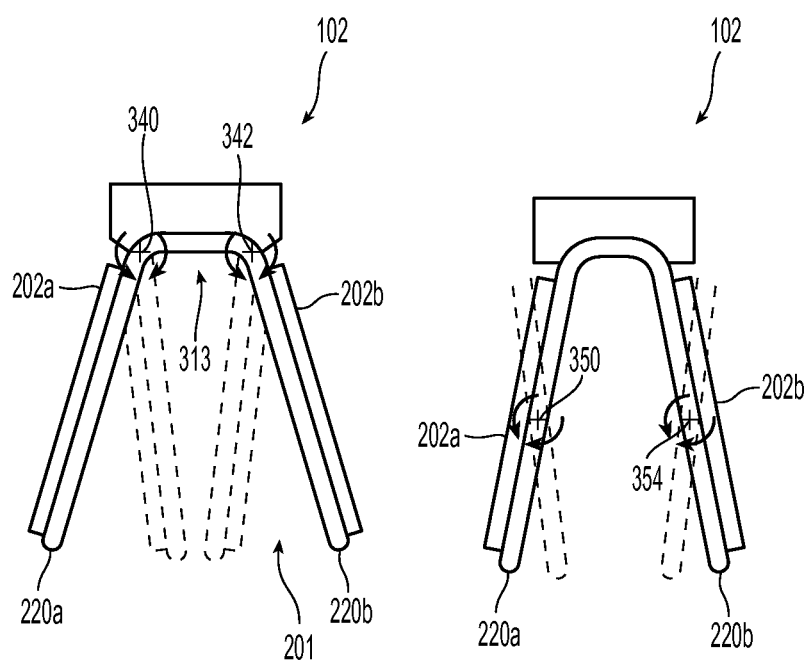
Fig. 10　　　　　Fig. 11

TREATMENT SYSTEMS WITH ADJUSTABLE GAP APPLICATORS AND METHODS FOR COOLING TISSUE

CROSS-REFERENCE TO RELATED APPLICATION

This application claims the benefit under 35 U.S.C. § 119(e) of U.S. Provisional Patent Application No. 61/992,813 filed May 13, 2014, which is incorporated by reference in its entirety.

INCORPORATION BY REFERENCE OF COMMONLY-OWNED APPLICATIONS AND PATENTS

The following commonly assigned U.S. Patent Applications and U.S. Patents are incorporated herein by reference in their entireties:

U.S. Patent Publication No. 2008/0287839 entitled "METHOD OF ENHANCED REMOVAL OF HEAT FROM SUBCUTANEOUS LIPID-RICH CELLS AND TREATMENT APPARATUS HAVING AN ACTUATOR";

U.S. Pat. No. 6,032,675 entitled "FREEZING METHOD FOR CONTROLLED REMOVAL OF FATTY TISSUE BY LIPOSUCTION";

U.S. Patent Publication No. 2007/0255362 entitled "CRYOPROTECTANT FOR USE WITH A TREATMENT DEVICE FOR IMPROVED COOLING OF SUBCUTANEOUS LIPID-RICH CELLS";

U.S. Pat. No. 7,854,754 entitled "COOLING DEVICE FOR REMOVING HEAT FROM SUBCUTANEOUS LIPID-RICH CELLS";

U.S. Patent Publication No. 2011/0066216 entitled "COOLING DEVICE FOR REMOVING HEAT FROM SUBCUTANEOUS LIPID-RICH CELLS";

U.S. Patent Publication No. 2008/0077201 entitled "COOLING DEVICES WITH FLEXIBLE SENSORS";

U.S. Patent Publication No. 2008/0077211 entitled "COOLING DEVICE HAVING A PLURALITY OF CONTROLLABLE COOLING ELEMENTS TO PROVIDE A PREDETERMINED COOLING PROFILE";

U.S. Patent Publication No. 2009/0118722, filed Oct. 31, 2007, entitled "METHOD AND APPARATUS FOR COOLING SUBCUTANEOUS LIPID-RICH CELLS OR TISSUE";

U.S. Patent Publication No. 2009/0018624 entitled "LIMITING USE OF DISPOSABLE SYSTEM PATIENT PROTECTION DEVICES";

U.S. Patent Publication No. 2009/0018623 entitled "SYSTEM FOR TREATING LIPID-RICH REGIONS";

U.S. Patent Publication No. 2009/0018625 entitled "MANAGING SYSTEM TEMPERATURE TO REMOVE HEAT FROM LIPID-RICH REGIONS";

U.S. Patent Publication No. 2009/0018627 entitled "SECURE SYSTEM FOR REMOVING HEAT FROM LIPID-RICH REGIONS";

U.S. Patent Publication No. 2009/0018626 entitled "USER INTERFACES FOR A SYSTEM THAT REMOVES HEAT FROM LIPID-RICH REGIONS";

U.S. Pat. No. 6,041,787 entitled "USE OF CRYOPROTECTIVE AGENT COMPOUNDS DURING CRYOSURGERY";

U.S. Pat. No. 8,285,390 entitled "MONITORING THE COOLING OF SUBCUTANEOUS LIPID-RICH CELLS, SUCH AS THE COOLING OF ADIPOSE TISSUE";

U.S. Provisional Patent Application Ser. No. 60/941,567 entitled "METHODS, APPARATUSES AND SYSTEMS FOR COOLING THE SKIN AND SUBCUTANEOUS TISSUE";

U.S. Pat. No. 8,275,442 entitled "TREATMENT PLANNING SYSTEMS AND METHODS FOR BODY CONTOURING APPLICATIONS";

U.S. patent application Ser. No. 12/275,002 entitled "APPARATUS WITH HYDROPHILIC RESERVOIRS FOR COOLING SUBCUTANEOUS LIPID-RICH CELLS";

U.S. patent application Ser. No. 12/275,014 entitled "APPARATUS WITH HYDROPHOBIC FILTERS FOR REMOVING HEAT FROM SUBCUTANEOUS LIPID-RICH CELLS";

U.S. Patent Publication No. 2010/0152824 entitled "SYSTEMS AND METHODS WITH INTERRUPT/RESUME CAPABILITIES FOR COOLING SUBCUTANEOUS LIPID-RICH CELLS";

U.S. Pat. No. 8,192,474 entitled "TISSUE TREATMENT METHODS";

U.S. Patent Publication No. 2010/0280582 entitled "DEVICE, SYSTEM AND METHOD FOR REMOVING HEAT FROM SUBCUTANEOUS LIPID-RICH CELLS";

U.S. Patent Publication No. 2012/0022518 entitled "COMBINED MODALITY TREATMENT SYSTEMS, METHODS AND APPARATUS FOR BODY CONTOURING APPLICATIONS";

U.S. Publication No. 2011/0238050 entitled "HOME-USE APPLICATORS FOR NON-INVASIVELY REMOVING HEAT FROM SUBCUTANEOUS LIPID-RICH CELLS VIA PHASE CHANGE COOLANTS, AND ASSOCIATED DEVICES, SYSTEMS AND METHODS";

U.S. Publication No. 2011/0238051 entitled "HOME-USE APPLICATORS FOR NON-INVASIVELY REMOVING HEAT FROM SUBCUTANEOUS LIPID-RICH CELLS VIA PHASE CHANGE COOLANTS, AND ASSOCIATED DEVICES, SYSTEMS AND METHODS";

U.S. Publication No. 2012/0239123 entitled "DEVICES, APPLICATION SYSTEMS AND METHODS WITH LOCALIZED HEAT FLUX ZONES FOR REMOVING HEAT FROM SUBCUTANEOUS LIPID-RICH CELLS";

U.S. patent application Ser. No. 13/830,413 entitled "MULTI-MODALITY TREATMENT SYSTEMS, METHODS AND APPARATUS FOR ALTERING SUBCUTANEOUS LIPID-RICH TISSUE";

U.S. patent application Ser. No. 13/830,027 entitled "TREATMENT SYSTEMS WITH FLUID MIXING SYSTEMS AND FLUID-COOLED APPLICATORS AND METHODS OF USING THE SAME";

U.S. patent application Ser. No. 11/528,225 entitled "COOLING DEVICE HAVING A PLURALITY OF CONTROLLABLE COOLING ELEMENTS TO PROVIDE A PREDETERMINED COOLING PROFILE;" and U.S. Pat. No. 8,285,390 entitled "MONITORING THE COOLING OF SUBCUTANEOUS LIPID-RICH CELLS, SUCH AS THE COOLING OF ADIPOSE TISSUE."

TECHNICAL FIELD

The present disclosure relates generally to treatment systems, applicators, and methods for removing heat from and/or adding heat to a subject. Several embodiments are directed to adjustable gap applicators that provide cooling/heating of targeted tissue.

BACKGROUND

Excess body fat, or adipose tissue, may be present in various locations of a subject's body, including, for example, the abdomen, thighs, buttocks, knees, back, face, arms, and other areas. Excess adipose tissue can detract from personal appearance and athletic performance. Moreover, excess adipose tissue is thought to magnify the unattractive appearance of cellulite, which forms when subcutaneous fat lobules protrude or penetrate into the dermis and create dimples where the skin is attached to underlying structural fibrous strands. Cellulite and excessive amounts of adipose tissue are often considered to be cosmetically unappealing. Diet and exercise may be insufficient to significantly reduce such excess adipose tissue.

Aesthetic improvement of the human body often involves the selective removal of adipose tissue. Invasive procedures, such as liposuction, tend to be associated with high costs, long recovery times, and increased risk of complications. In many instances, non-invasive or minimally invasive procedures can avoid some or all of these disadvantages while providing at least comparable clinical outcomes as those of invasive procedures. For example, non-invasive removal of excess subcutaneous adipose tissue can eliminate both unnecessary recovery time and discomfort associated with invasive procedures. Conventional non-invasive treatments for removing excess body fat typically include application of topical agents, use of weight-loss drugs, regular exercise, dieting, or a combination of these treatments. One drawback of these treatments is that they may not be effective or even possible under certain circumstances. For example, when a person is physically injured or ill, regular exercise may not be an option. Weight-loss drugs or topical agents are not an option if, as another example, they cause an allergic or negative reaction. Furthermore, fat loss in selective areas of a person's body often cannot be achieved using general or systemic weight-loss methods.

Other methods designed to reduce subcutaneous adipose tissue include applying energy to subcutaneous lipid-rich cells via, e.g., radio frequency and/or light energy, such as described in U.S. Patent Publication No. 2006/0036300 and U.S. Pat. No. 5,143,063, or via, e.g., high intensity focused ultrasound (HIFU) such as described in U.S. Pat. Nos. 7,258,674 and 7,347,855. Additional methods and devices for non-invasively reducing subcutaneous adipose tissue by cooling are disclosed in U.S. Pat. No. 7,367,341 entitled "METHODS AND DEVICES FOR SELECTIVE DISRUPTION OF FATTY TISSUE BY CONTROLLED COOLING" to Anderson et al. and U.S. Patent Publication No. 2005/0251120 entitled "METHODS AND DEVICES FOR DETECTION AND CONTROL OF SELECTIVE DISRUPTION OF FATTY TISSUE BY CONTROLLED COOLING" to Anderson et al., the entire disclosures of which are incorporated herein by reference.

BRIEF DESCRIPTION OF THE DRAWINGS

In the drawings, identical reference numbers identify similar elements or acts.

FIGS. 7-11 are a series of schematic views of an adjustable gap applicator in different configurations in accordance with various embodiments of the technology.

DETAILED DESCRIPTION

A. Overview

Figure 1:
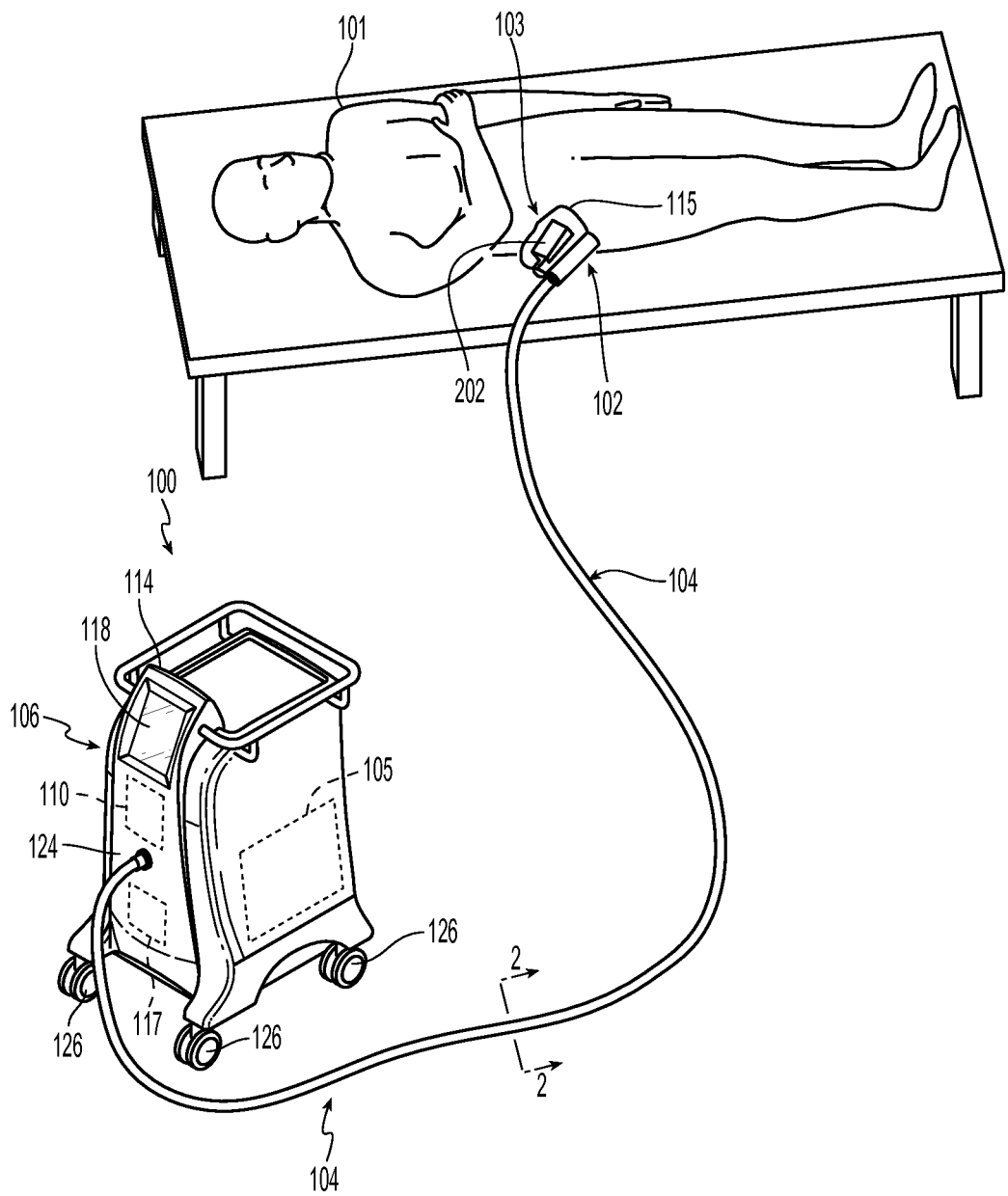
FIG. 1 is a partially schematic, isometric view of a treatment system for non-invasively affecting target regions of a subject in accordance with an embodiment of the technology.

The present disclosure describes treatment systems, applicators, and methods for affecting targeted tissue. Several of the details set forth below are provided to describe the following examples and methods in a manner sufficient to enable a person skilled in the relevant art to practice, make, and use them. Several of the details and advantages described below, however, may not be necessary to practice certain examples and methods of the technology. Additionally, the technology may include other examples and methods that are within the scope of the technology but are not described in detail.

At least some embodiments of the present technology can include treatment systems for affecting tissue in a target region of a human subject. The term "treatment system", as used generally herein, refers to cosmetic or medical treatment systems, as well as any treatment regimens or medical device usage. The treatment system can reduce or eliminate excess adipose tissue, love handles, saddlebags, or other undesired body features associated with excessive tissue that can be drawn into an applicator. The shape, size, and/or dimensions of a gap and/or tissue-receiving cavity of the applicator can be adjusted to affect treatment.

In some embodiments, a system for treating subcutaneous lipid-rich cells of a subject includes a vacuum applicator with a tissue-receiving cavity, a vacuum port that provides a vacuum to draw the subject's tissue into the tissue-receiving cavity, and a thermal element. The thermal element can be configured for heat transfer with the subject's tissue that has been drawn into the tissue-receiving cavity to affect subcutaneous lipid-rich cells. The vacuum applicator can also include an adjustment mechanism with different modes of operation. In an expansion mode, the adjustment mechanism can widen the cavity until the vacuum applicator is in an expanded gentle tissue draw configuration. In a contraction mode, the adjustment mechanism can narrow the cavity to increase thermal contact between the thermal element and the tissue (e.g., tissue located in the cavity). In some embodiments, the cavity in the gentle tissue draw configuration can have a preset first volume, and the cavity in a narrowed or high thermal contact configuration has a preset second volume that is less than the preset first volume.

In one embodiment, a system for treating subcutaneous lipid-rich cells of a subject includes a vacuum applicator configured to receive the subject's tissue. The vacuum applicator includes a vacuum cup that defines at least a portion of a tissue-receiving cavity or gap, at least one thermal element configured for heat transfer with the subject's tissue that has been drawn into the tissue-receiving cavity or gap, and an entrance opening that narrows to compress the subject's tissue, which is located in the entrance opening, more than the subject's tissue that has been drawn into the tissue-receiving cavity or gap. In some embodiments, the system further includes an adjustment mechanism operable to reconfigure the vacuum applicator to mechanically urge the subject's tissue deeper into the tissue-receiving cavity. In an expansion mode, the adjustment mechanism can widen the entrance opening. In a contraction mode, the adjustment mechanism can narrow the entrance opening.

Some of the embodiments disclosed herein can be for cosmetically beneficial alterations of a variety of body regions. Some treatment procedures may be for the sole purpose of altering the body region to conform to a cosmetically desirable look, feel, size, shape or other desirable cosmetic characteristic or feature. Accordingly, at least some embodiments of the cosmetic procedures can be performed without providing an appreciable therapeutic effect (e.g., no therapeutic effect). For example, some treatment procedures may not include restoration of health, physical integrity, or the physical well-being of a subject. The cosmetic methods can target subcutaneous regions to change a subject's appearance and can include, for example, procedures performed on a subject's love handles (i.e., excess adipose tissue at the sides of a subject's waistline). In other embodiments, however, the cosmetically desirable treatments may have therapeutic outcomes (whether intended or not), such as psychological benefits, alteration of body hormones levels (by the reduction of adipose tissue), etc.

Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, stages, or characteristics may be combined in any suitable manner in one or more examples of the technology. The headings provided herein are for convenience only and are not intended to limit or interpret the scope or meaning of the technology.

B. Cryotherapy

FIG. 1 and the following discussion provide a brief, general description of a treatment system 100 in accordance with some embodiments of the technology. The treatment system 100 can be a temperature-controlled system for exchanging heat with a subject 101 and can include an adjustable gap applicator 102 ("applicator 102") configured selectively to cool targeted tissue. The applicator 102 can be manually or automatically moved between different configurations to, for example, comfortably draw tissue into the applicator 102, increase the depth of tissue draw, and/or manipulate tissue (e.g., compress and/or massage tissue within the applicator 102). The applicator 102 can have one or more selectively movable features for adjusting the size and/or shape of a tissue-receiving gap or cavity of the applicator 102 any number of times before, during, and/or after selectively heating/cooling targeted tissue. The movable features can include, for example, sidewalls, thermal elements, panels, and/or other features that can be moved to affect treatment.

Without being bound by theory, the selective effect of cooling is believed to result in, for example, membrane disruption, cell shrinkage, disabling, damaging, destroying, removing, killing or other methods of lipid-rich cell alteration. Such alteration is believed to stem from one or more mechanisms acting alone or in combination. It is thought that such mechanism(s) trigger an apoptotic cascade, which is believed to be the dominant form of lipid-rich cell death by non-invasive cooling. In any of these embodiments, the effect of tissue cooling is to selectively reduce lipid-rich cells by a desired mechanism of action, such as apoptosis, lipolysis, or the like. In some procedures, the applicator 102 can cool the tissue to a temperature in a range of from about −25° C. to about 20° C., about −40° C. to about 10° C., or other suitable ranges. In other embodiments, the cooling temperatures can be from about −40° C. to about 10° C., from about −20° C. to about 10° C., from about −18° C. to about 5° C., from about −15° C. to about 5° C., or from about −15° C. to about 0° C. In further embodiments, the cooling temperatures can be equal to or less than about −5° C., −10° C., −15° C. Other target cooling temperatures can be used.

Apoptosis, also referred to as "programmed cell death", is a genetically-induced death mechanism by which cells self-destruct without incurring damage to surrounding tissues. An ordered series of biochemical events induce cells to morphologically change. These changes include cellular blebbing, loss of cell membrane asymmetry and attachment, cell shrinkage, chromatin condensation and chromosomal DNA fragmentation. Injury via an external stimulus, such as cold exposure, is one mechanism that can induce cellular apoptosis in cells. Nagle, W. A., Soloff, B. L., Moss, A. J. Jr., Henle, K. J. "Cultured Chinese Hamster Cells Undergo Apoptosis After Exposure to Cold but Nonfreezing Temperatures" Cryobiology 27, 439-451 (1990).

One aspect of apoptosis, in contrast to cellular necrosis (a traumatic form of cell death causing local inflammation), is that apoptotic cells express and display phagocytic markers on the surface of the cell membrane, thus marking the cells for phagocytosis by macrophages. As a result, phagocytes can engulf and remove the dying cells (e.g., the lipid-rich cells) without eliciting an immune response. Temperatures that elicit these apoptotic events in lipid-rich cells may contribute to long-lasting and/or permanent reduction and reshaping of subcutaneous adipose tissue.

One mechanism of apoptotic lipid-rich cell death by cooling is believed to involve localized crystallization of lipids within the adipocytes at temperatures that do not induce crystallization in non-lipid-rich cells. The crystallized lipids selectively may injure these cells, inducing apoptosis (and may also induce necrotic death if the crystallized lipids damage or rupture the bi-lipid membrane of the adipocyte). Another mechanism of injury involves the lipid phase transition of those lipids within the cell's bi-lipid membrane, which results in membrane disruption or dysfunction, thereby inducing apoptosis. This mechanism is well-documented for many cell types and may be active when adipocytes, or lipid-rich cells, are cooled. Mazur, P., "Cryobiology: the Freezing of Biological Systems" Science, 68: 939-949 (1970); Quinn, P. J., "A Lipid Phase Separation Model of Low Temperature Damage to Biological Membranes" Cryobiology, 22: 128-147 (1985); Rubinsky, B., "Principles of Low Temperature Preservation" Heart Failure Reviews, 8, 277-284 (2003). Other possible mechanisms of adipocyte damage, described in U.S. Pat. No. 8,192,474, relate to ischemia/reperfusion injury that may occur under certain conditions when such cells are cooled as described herein. For instance, during treatment by cooling as described herein, the targeted adipose tissue may experience a restriction in blood supply and thus be starved of oxygen due to isolation as a result of applied pressure, cooling which may affect vasoconstriction in the cooled tissue, or the like. In addition to the ischemic damage caused by oxygen starvation and the buildup of metabolic waste products in the tissue during the period of restricted blood flow, restoration of blood flow after cooling treatment may additionally produce reperfusion injury to the adipocytes due to inflammation and oxidative damage that is known to occur when oxygenated blood is restored to tissue that has undergone a period of ischemia. This type of injury may be accelerated by exposing the adipocytes to an energy source (via, e.g., thermal, electrical, chemical, mechanical, acoustic, or other means) or otherwise increasing the blood flow rate in connection with or after cooling treatment as described herein. Increasing vasoconstriction in such adipose tissue by, e.g., various mechanical means (e.g., application of pressure or massage), chemical means or certain cooling conditions, as well as the local introduction of oxygen radical-forming compounds to stimulate inflammation and/or leukocyte activity in adipose tissue may also contribute to accelerating injury to such cells. Other yet-to-be understood mechanisms of injury may exist.

In addition to the apoptotic mechanisms involved in lipid-rich cell death, local cold exposure is also believed to induce lipolysis (i.e., fat metabolism) of lipid-rich cells and has been shown to enhance existing lipolysis which serves to further increase the reduction in subcutaneous lipid-rich cells. Vallerand, A. L., Zamecnik. J., Jones, P. J. H., Jacobs, I. "Cold Stress Increases Lipolysis, FFA Ra and TG/FFA Cycling in Humans" Aviation, Space and Environmental Medicine 70, 42-50 (1999).

One expected advantage of the foregoing techniques is that the subcutaneous lipid-rich cells in the target region can be reduced generally without collateral damage to non-lipid-rich cells in the same region. In general, lipid-rich cells can be affected at low temperatures that do not affect non-lipid-rich cells. As a result, lipid-rich cells, such as those associated with cellulite, love handles, muffin tops, saddlebags, etc., can be affected while other cells in the same region generally are not damaged even though the non-lipid-rich cells at the surface (e.g., cells in the dermis and/or epidermis) may be subjected to even lower temperatures than those to which the lipid-rich cells are exposed.

Tissue can be rapidly heated and cooled any number of times in different sequences selected based on the procedure to be performed. Periods of heating/cooling can be equal to or less than about 1 minute, 2 minutes, 3 minutes, 5 minutes, 10 minutes, 20 minutes, 1 hour, 70 minutes, etc. An initial precooling or preheating cycle can be performed to prepare the treatment site for a low temperature cooling cycle. In an initial cooling cycle, tissue can be cooled to a temperature below 37° C. (e.g., to a temperature between about −40° C. to about 30° C., between about −30° C. to about 25° C., or between about −20° C. to about 20° C.). In some preheating cycles, tissue can be heated for a period of time (e.g., 1 minute, 2 minutes, 2.3 minutes, 3 minutes, 5 minutes) to a first temperature (e.g., 30° C., 35° C., 40° C., etc.). The initial precooling or preheating cycles can include cooling or heating tissue at constant or varying rates. After the preheating cycle, the tissue can be cooled to a lower temperature (e.g., 2° C., −5° C., −10° C., −13° C., −20° C.) for a cooling period of about 30 minutes, 40 minutes, about 50 minutes, about 1 hour, about 70 minutes, about 80 minutes, etc. After cooling the tissue, the applicator can be actively or passively returned to body or room temperature. For example, thermoelectric elements of the applicator can naturally return to body or room temperature prior to removing the applicator.

In some procedures, the applicator 102 can remove heat from the underlying tissue through the upper layers of the skin and create a thermal gradient with the coldest temperatures near the cooling surface, or surfaces, of the applicator 102 (i.e., the temperature of the upper layer(s) of the skin can be lower than that of the targeted underlying cells). It may be challenging to reduce the temperature of the deep cells (e.g., lipid-rich cells) low enough to be destructive to these target cells (e.g., induce apoptosis, cell death, etc.) while also maintaining the temperature of the upper and surface skin cells high enough so as to be protective (e.g., non-destructive). The temperature difference between these two thresholds can be small (e.g., about 5° C. to about 10° C., less than 10° C., less than 15° C., etc.). Protection of the overlying cells (e.g., typically water-rich dermal and epidermal skin cells) from freeze damage during dermatological and related aesthetic procedures that require sustained exposure to cold temperatures may include improving the freeze tolerance and/or freeze avoidance of these skin cells. Cryoprotectants can be used to inhibit or prevent such freeze damage.

C. Treatment Systems

FIG. 1 shows the treatment system 100 that includes the applicator 102, a connector 104, and a control module 106. The applicator 102 can include a conformable vacuum cup 115 and one or more thermal elements 202 for cooling tissue that has been drawn into the vacuum cup 115. The connector 104 can provide energy (e.g., electrical energy) and fluid (e.g., coolant) from the control module 106 to the applicator 102. An operator can use the control module 106 to control operation of the applicator 102 to non-invasively remove heat from targeted areas of the subject 101, such as an abdominal area 103 or another suitable area.

Figure 2:
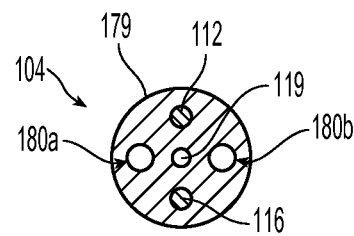
FIG. 2 is a cross-sectional view of a connector taken along line 2-2 of FIG. 1.

FIG. 2 is a cross-sectional view of the connector 104 taken along line 2-2 of FIG. 1 in accordance with at least some embodiments of the technology. The connector 104 can include a main body 179, a supply fluid line or lumen 180a ("supply fluid line 180a"), and a return fluid line or lumen 180b ("return fluid line 180b"). The main body 179 may be configured (via one or more adjustable joints) to "set" in place for the treatment of the subject 101. The supply and return fluid lines 180a, 180b can be conduits comprising, in whole or in part, polyethylene, polyvinyl chloride, polyurethane, and/or other materials that can accommodate circulating coolant, such as water, glycol, synthetic heat transfer fluid, oil, refrigerant, and/or any other suitable heat conducting fluid. In one embodiment, each fluid line 180a, 180b can be a flexible hose surrounded by the main body 179. The connector 104 can also include one or more electrical lines 112 for providing power to the applicator 102 and one or more control lines 116 for providing communication between the control module 106 (FIG. 1) and the applicator 102 (FIG. 1). In various embodiments, the connector 104 can include a bundle of fluid conduits, a bundle of power lines, wired connections, and other bundled and/or unbundled components selected to provide ergonomic comfort, minimize unwanted motion (and thus potential inefficient removal of heat from the subject 101), and/or to provide an aesthetic appearance to the treatment system 100.

Referring again to FIG. 1, the control module 106 can include a fluid chamber or reservoir 105 (illustrated in phantom line), a power supply 110 (illustrated in phantom line), and a controller 114 carried by a housing 124 with wheels 126. The control module 106 can include a refrigeration unit, a cooling tower, a thermoelectric chiller, heaters, or any other device capable of controlling the temperature of coolant in the fluid chamber 105. The coolant can be continuously or intermittently delivered to the applicator 102 via the supply fluid line 180a (FIG. 2) and can circulate through the applicator 102 to absorb heat. The coolant, which has absorbed heat, can flow from the applicator 102 back to the control module 106 via the return fluid line 180b (FIG. 2). For warming periods, the control module 106 can heat the coolant such that warm coolant is circulated through the applicator 102. Alternatively, a municipal water supply (e.g., tap water) can be used in place of or in conjunction with the control module 106. A pressurization device 117 can provide suction to the applicator 102 via a vacuum line 119 (FIG. 2) and can include one or more pumps. Air pressure can either be controlled with a regulator between the pressurization device 117 and the applicator 102, or pressure may be reduced up to the maximum capacity of the pressurization device 117. If the vacuum level is too low, the tissue will not be drawn adequately (or at all) inside the applicator 102. If the vacuum level is too high, undesirable discomfort to the patient and/or tissue damage could occur. According to one embodiment, approximately 3 inches Hg, 5 inches Hg, or 7 inches Hg of vacuum is applied; in alternative embodiments, other vacuum levels can be applied.

An operator can control operation of the treatment system 100 using an input/output device 118 of the controller 114. The input/output device 118 can display the configuration and state of operation of the applicator 102. The power supply 110 can provide a direct current voltage for powering electrical elements of the applicator 102 via the line 112 (FIG. 2). In some embodiments, the controller 114 can exchange data with the applicator 102 via a wireless or an optical communication link and can monitor and adjust treatment based on one or more treatment profiles and/or patient-specific treatment plans, such as those described, for example, in commonly assigned U.S. Pat. No. 8,275,442. Each treatment profile can include one or more segments, and each segment can include applicator settings (e.g., gap dimensions, dimensions of a tissue-receiving cavity in the applicator 102, etc.), vacuum levels, specified durations (e.g., 10 minutes, 30 minutes, 1 hour, 2 hours, etc.), a target profile, etc. For example, treatment profiles can include one or more protocols for drawing tissue into the applicator 102, protocols for manipulating tissue in the applicator 102, massage protocols, protocols for adjusting vacuum levels, or other treatment protocols. The controller 114 can contain instructions for switching the applicator 102 between different modes (e.g., an expansion mode, a contraction mode, a heating/cooling mode, a massage mode, etc.) based on one or more signals from one or more detectors, such as a draw depth detector. Additionally, if the treatment system 100 includes multiple applicators, the treatment profile can include specific profiles for each applicator to concurrently treat sites.

D. Applicators and Methods of Treatment

Figure 3:
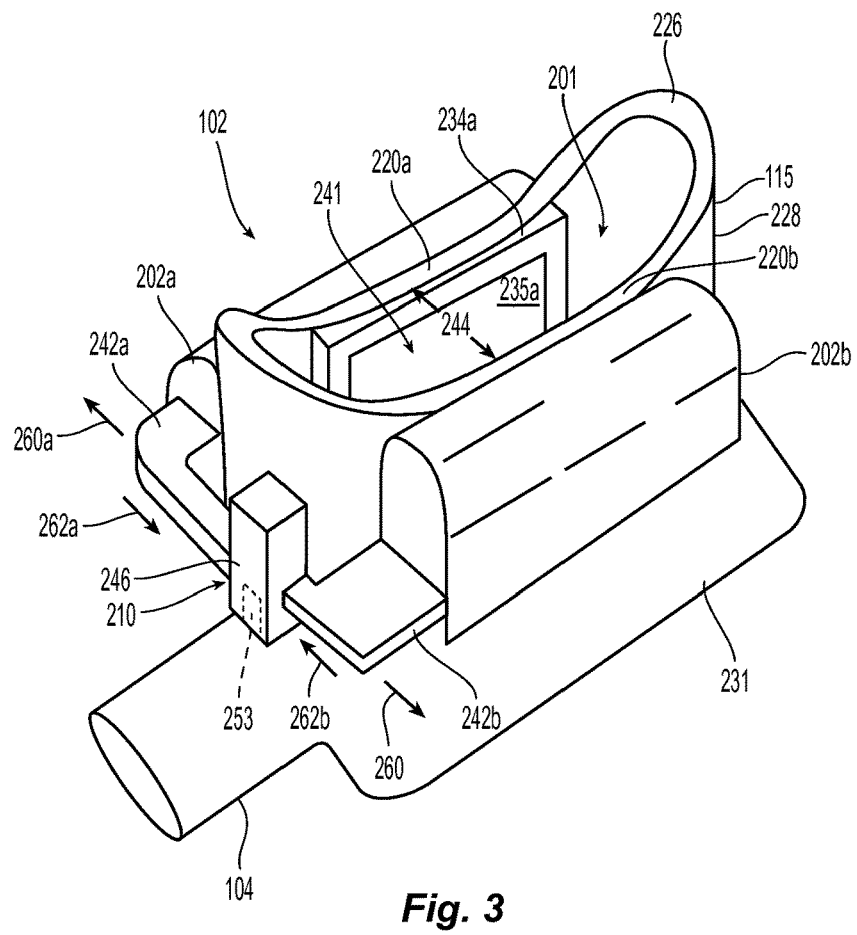
FIG. 3 is an isometric view of an adjustable gap applicator in accordance with an embodiment of the technology.

FIG. 3 is an isometric view of the applicator 102 in accordance with an embodiment of the technology. The applicator 102 can include a tissue-receiving cavity 201 ("cavity 201"), thermal elements 202a, 202b (collectively, "thermal elements 202"), the vacuum cup 115, and a cavity or gap adjustment mechanism 210. The thermal elements 202 are positioned to transfer heat with tissue that has been drawn into the cavity 201. The adjustment mechanism 210 can simultaneously or sequentially move sidewalls 220a, 220b (collectively "sidewalls 220") before, during, and/or after a tissue draw process. In some embodiments, the adjustment mechanism 210 has an expansion mode for expanding the cavity 201 to a gentle tissue draw configuration for receiving tissue and a contraction mode to, for example, compress tissue, increase thermal contact between the thermal elements 202 and tissue, and/or otherwise enhance treatment.

Throughout this document, the description of one thermal element 202a or 202b applies to the other thermal element 202a or 202b. The thermal element 202a can include a conductive member 234a and a covering 235a. The conductive member 234a can be flat or shaped (e.g., curved) and can be made, in whole or in part, of metal or other conductive material (e.g., a rigid conductive material, a flexible conductive material, etc.), and the covering 235a can be a film, a sheet, a sleeve, or other component suitable for defining an interface surface. In various embodiments, the thermal element 202a can include, without limitation, one or more thermoelectric elements (e.g., Peltier-type elements), fluid-cooled elements, heat-exchanging units, or combinations thereof. For example, each thermal element 202 can include an array of thermoelectric elements for heating/cooling tissue and one or more fluid-cooled elements for cooling the thermoelectric elements. The fluid-cooled elements can exchange heat with the backside of the thermoelectric elements to keep the thermoelectric elements at or below target temperatures. In other embodiments, the thermal elements 202 can comprise only fluid-cooled elements or only non-fluid cooled thermoelectric elements. The configurations and components of the thermal elements 202 can be selected based on the desired power consumption and targeted temperatures. Although the illustrated applicator 102 has two thermal elements 202, the applicator 102 may include any number of thermal elements 202 or cooling surfaces disposed at discrete locations anywhere around the cavity 201. In other embodiments, the applicator 102 may be provided with a single thermal element 202.

The vacuum cup 115 can include a lip 226 and a main body 228. The lip 226 can be rounded to comfortably contact the patient's tissue and can define an entrance opening 241. The main body 228 can extend between the lip 226 and a base module 231 and can have a one-piece or multi-piece construction. In some relatively highly compliant embodiments, the vacuum cup 115 can be made, in whole or in part, of rubber, soft plastic, or other suitable material. The mechanical properties, thermal properties, shape, and/or dimensions of the vacuum cup 115 can be selected based on, for example, target treatment sites, target treatment temperatures, and desired volume of tissue to be drawn into the cavity 201.

The adjustment mechanism 210 can change the configuration of the applicator 102 by, for example, moving the thermal elements 202 and/or the vacuum cup 115 and can include a drive device 246, arms 242a, 242b, and a sensor 253. The drive device 246 can include, without limitation, one or more drive motors (e.g., stepper motors), solenoids, drive mechanisms (e.g., screw drive mechanisms), lever mechanisms, cam devices, motion devices (e.g., pistons, linkages, linear slides, etc.), closure devices (e.g., caliper closures, clamp closures, or cam actuated closures), and/or other components capable of translating and/or rotating the arms 242a, 242b to achieve a wide range of different types of motion (e.g., linear and/or rotary motion of features of the applicator 102). The sensor 253 can include a potentiometer, an encoder (e.g., an optical encoder), a proximity sensor (e.g., an optical proximity sensor), or the like. In one embodiment, the sensor 253 is a sensor for measuring rotation of a rotational drive mechanism (e.g., screw-drive mechanism) of the drive device 246 and can be in communication with the control module 106 (FIG. 1) via the control line 116 (FIG. 2) or a wireless network. In other embodiments, the sensor 253 is a displacement sensor calibrated to the width (or other dimension) of the gap 244 and/or cavity 201. Sensors can be at other locations to detect the configuration and dimensions of the gap 244 and/or cavity 201 and/or other information usable to modify treatment.

Figure 4:
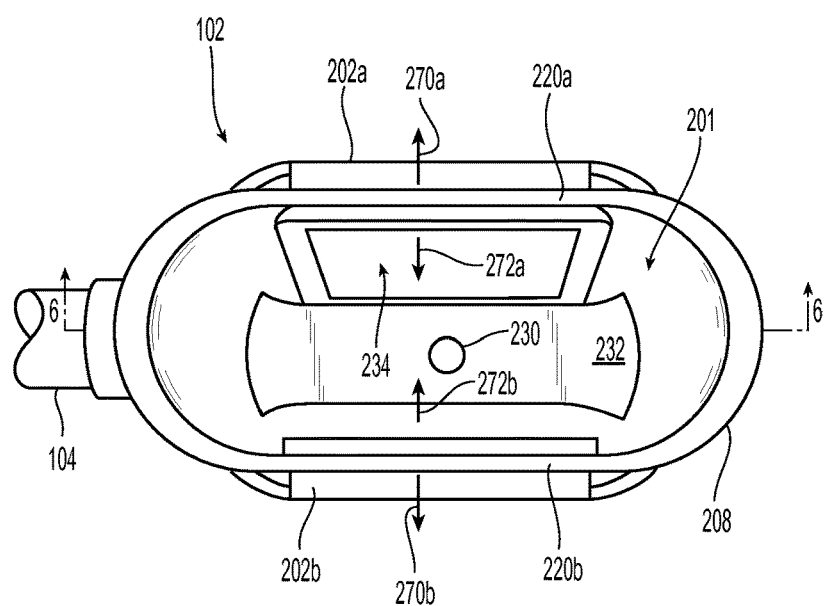
FIG. 4 is a plan view of the applicator of FIG. 3.

FIG. 4 is a plan view of the applicator 102 in accordance with embodiments of the technology. Referring now to FIGS. 3 and 4, when the adjustment mechanism 210 (FIG. 3) is in an expansion mode, the drive device 246 can drive the arms 242a, 242b away from one another (indicated by arrows 260a, 260b in FIG. 3) to drive the thermal elements 202a, 202b away from one another (indicated by arrows 270a, 270b of FIG. 4). When the adjustment mechanism 210 (FIG. 3) is in a contraction mode, the drive device 246 can drive the arms 242a, 242b toward one another (indicated by arrows 262a, 262b of FIG. 3) to drive the thermal elements 202a, 202b toward one another (indicated by arrows 272a, 272b of FIG. 4). When the adjustment mechanism 210 is locked, it can hold the thermal elements 202a, 202b stationary relative to one another.

FIG. 4 shows a single vacuum port 230 positioned at a bottom 232 of the cavity 201. The vacuum port 230 is configured to provide a desired vacuum level to draw the subject's tissue into the cavity 201. If the vacuum level is too low, tissue will not be drawn adequately (or at all) into the cavity 201. If the vacuum level is too high, undesirable discomfort to the patient and/or tissue damage could occur. The number and locations of the vacuum ports can be selected based on, e.g., the amount of tissue draw desired, considerations of patient comfort, and the desired vacuum level.

Figure 5:
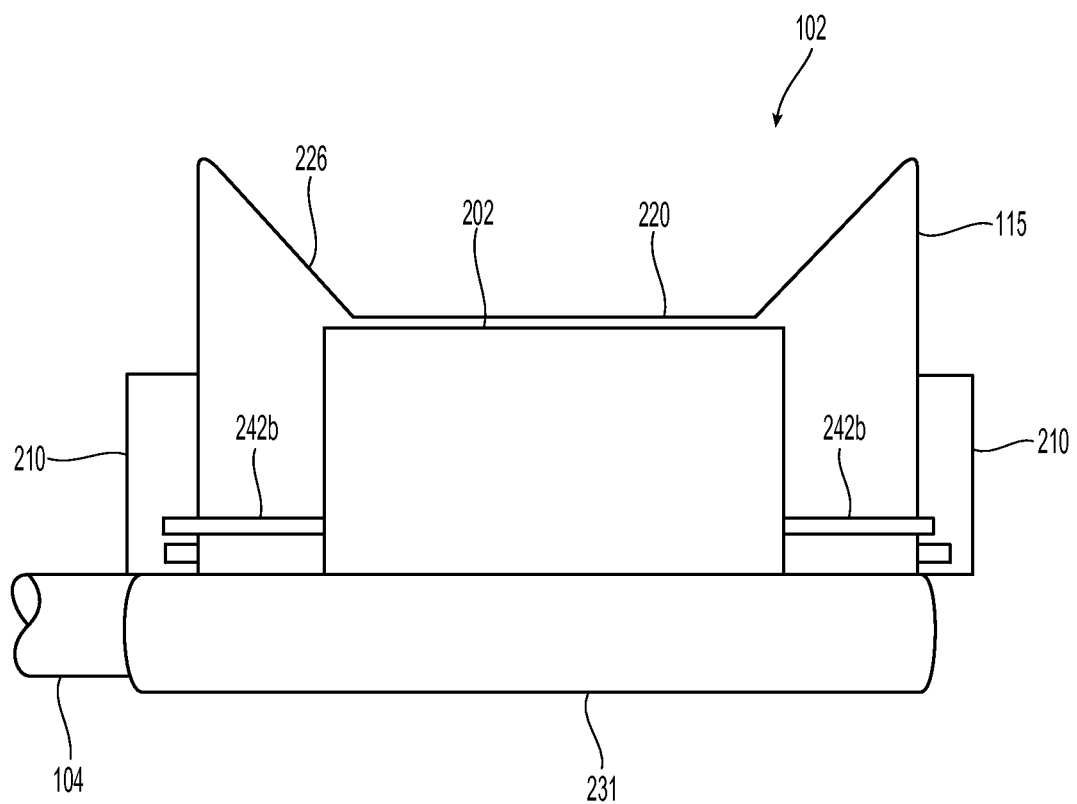
FIG. 5 is a side view of the applicator of FIG. 3.

FIG. 5 is a side view of the applicator 102. Adjustment mechanisms 210 can be positioned at opposite ends of the vacuum cup 115 to provide independent movement of the ends of the thermal elements 202 to mechanically urge tissue deeper into the cavity. The base module 231 can include, without limitation, circuitry, memory, or other electrical components for controlling the adjustment mechanisms 210.

Figure 6:
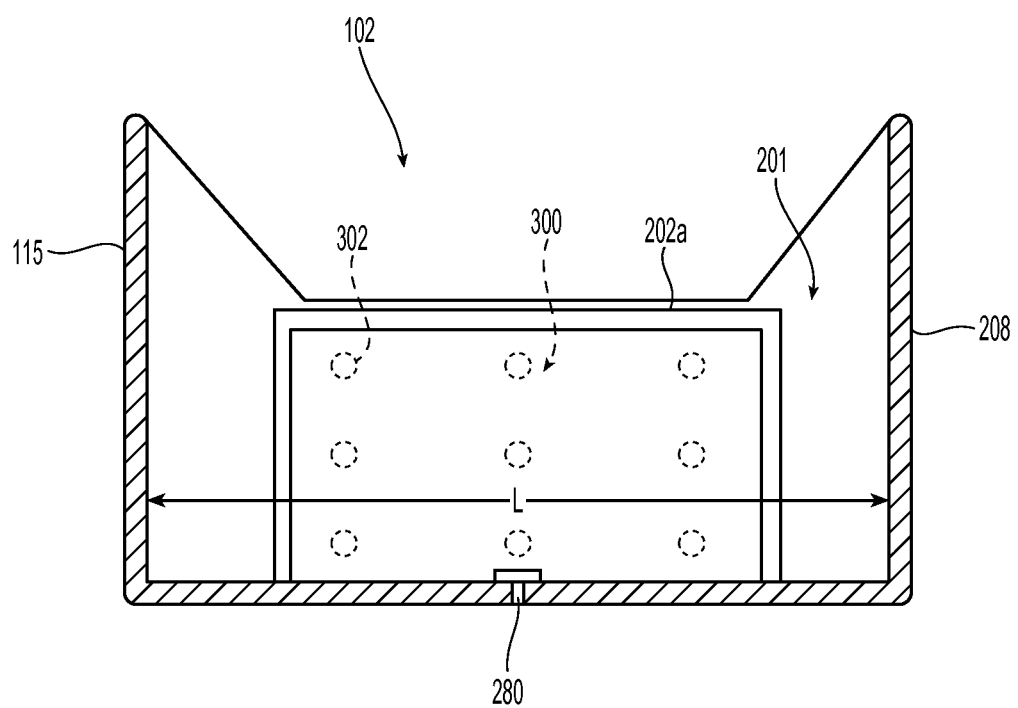
FIG. 6 is a cross-sectional view of the applicator taken along line 6-6 of FIG. 4.

FIG. 6 is a cross-sectional view of components of the applicator 102 taken along line 6-6 of FIG. 4. The applicator 102 can include a tissue draw depth detector 300 configured to determine the depth that tissue has been drawn into the cavity 201. The draw depth detector 300 can include an array of evenly or unevenly spaced apart sensors 302 (one identified in FIG. 6). The sensors 302 can be coupled to the surface of the thermal element 202a, embedded in the thermal element 202a, or located at other suitable positions, including along the vacuum cup 115. The illustrated embodiment includes nine sensors 302, but a greater or lesser number of sensors can be used, if any. For example, the thermal element 202a can include multiple cooling plates, each cooling plate containing or carrying one or more sensors.

The sensors 302 can be temperature sensors (e.g., thermistors) positioned to detect temperature changes associated with warm tissue being drawn into the cavity 201. The control module 106 (FIG. 1) can interpret the detected temperature increase associated with skin contact and can determine the depth of tissue draw based on the locations and amount of temperature increase. In some procedures, the thermal element 202a can be at a relative low temperature (e.g., a temperature in the range of between about −20° C. to about 5° C.) to enhance detection of the presence of tissue. In some embodiments, the sensors 302 measure heat flux and/or pressure (e.g., contact pressure) with the skin of the patient and can be located anywhere along the cavity 201. In yet further embodiments, the sensors 302 can be tissue impedance sensors or other sensors capable of detecting the presence and/or characteristics of tissue. The sensors 302 can also be contact sensors, air volume sensors, optical depth sensors, and/or imaging devices. Feedback from the sensors 302 can be collected in real-time. Real-time collection and processing of such feedback can be used in concert with treatment administration to efficaciously alter or reduce subcutaneous adipose tissue and/or control freeze events. The sensor measurements can indicate other changes or anomalies that can occur during treatment administration. For example, an increase in temperature detected by one or more sensors 302 can indicate a freezing event at the skin or underlying tissue (i.e., dermal tissue). An increase in temperature as detected by the sensors 302 can also indicate movement associated with the applicator 102. Methods and systems for collection of feedback data and monitoring of temperature measurements are described in commonly assigned U.S. Pat. No. 8,285,390.

FIGS. 7-11 are a series of views of the applicator 102 in different configurations. The positions and orientations of the sidewalls 220 and/or thermal elements 202 can be adjusted. Translation of the sidewalls 220 is discussed in connection with FIGS. 7-9, and rotation of the sidewalls 220 is discussed in connection with FIGS. 10 and 11. Referring now to FIG. 7, the applicator 102 is in a treatment configuration for heating/cooling tissue. FIG. 8 shows the applicator 102 in an expanded or tissue draw configuration after the sidewalls 220a, 220b have been translated outwardly (indicated by arrows 317, 319 in FIG. 7). FIG. 9 shows the applicator 102 in a tissue compression configuration after the sidewalls 220a, 220b have been translated inwardly (indicated by arrows 321, 323 in FIG. 7).

Referring to FIGS. 5 and 10 together, the adjustment mechanisms 210 (FIG. 5) can rotate the sidewalls 220a, 220b about axes of rotation 340, 342 (FIG. 10) located near the bottom or base 313 of the cavity 201. In some embodiments, the sidewalls 220a, 220b can be rotated from a first angular position (shown in solid line) to a second angular position (shown in phantom line). The sidewalls 220a, 220b in the first angular position can define positive draft angles, and the sidewalls 220a, 220b in the second angular position can be generally parallel or define negative draft angles. Referring now to FIG. 11, the adjustment mechanisms 210 (FIG. 5) can rotate the sidewalls 220a, 220b about axes of rotation 350, 354 between a splayed-out arrangement (shown in solid line), negative draft angle arrangement (shown in phantom line), generally parallel arrangement, or other desired arrangement.

FIGS. 12-15 are a series of views of a method of performing cryotherapy in accordance with various embodiments of the present technology. Generally, tissue can be drawn into the expanded applicator 102. The expanded configuration of the applicator 102 allows a relative large volume of tissue to be drawn into the cavity 201. The applicator 102 can assume a relatively narrowed configuration so to compress the tissue within the cavity 201 and cool/heat the compressed tissue. The vacuum level can be reduced and/or the applicator 102 can be expanded to release the tissue.

Figure 12:
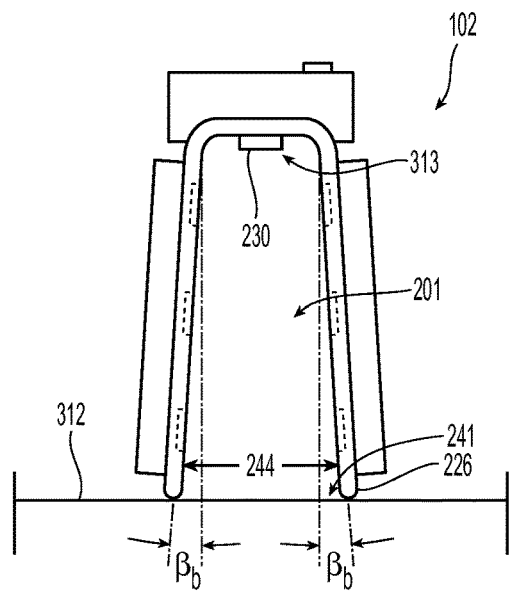
FIGS. 12-15 are a series of views of methods of performing cryotherapy in accordance with embodiments of the technology.
Figure 13:
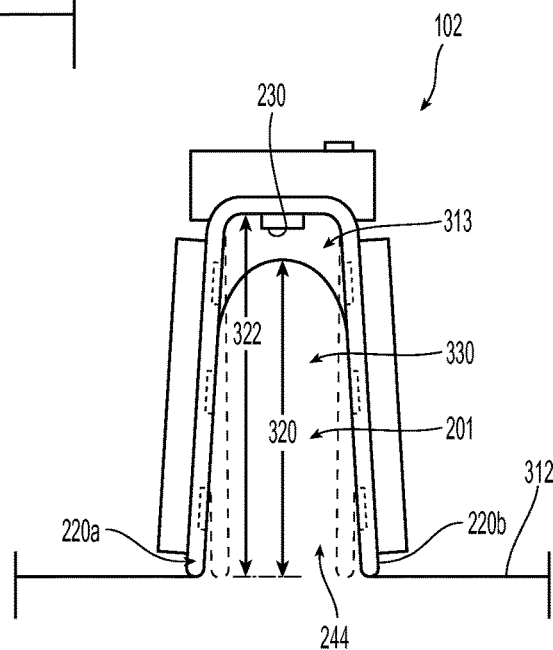

When the applicator 102 is in the gentle tissue draw configuration shown in FIGS. 12 and 13, a distance between opposite faces of the cavity 201, or width of the gap 244, can be in a range of about 44 mm (1.7 inches) to about 58 mm (2.2 inches). The distance or width can be reduced a preselected distance (e.g., 6 mm to 20 mm) or percentage (e.g., 10%, 15%, or 20%). When the applicator 102 is in the treatment configuration (FIG. 14), a distance between opposite faces of the cavity 201, or the width of the gap 244, can be between approximately 0.5 and 3 inches or more may be desired. In some procedures, the width of the gap 244 (FIG. 14) is in a range of about 1.3 inches to about 1.7 inches. In one procedure, the width of the gap 244 is about 1.5 inches (38 mm). In alternative embodiments, the gap 244 and/or cavity 201 can have other dimensions, configurations, etc. Various details of operation of the applicator 102 and cryotherapy are discussed in detail below.

Figure 14:
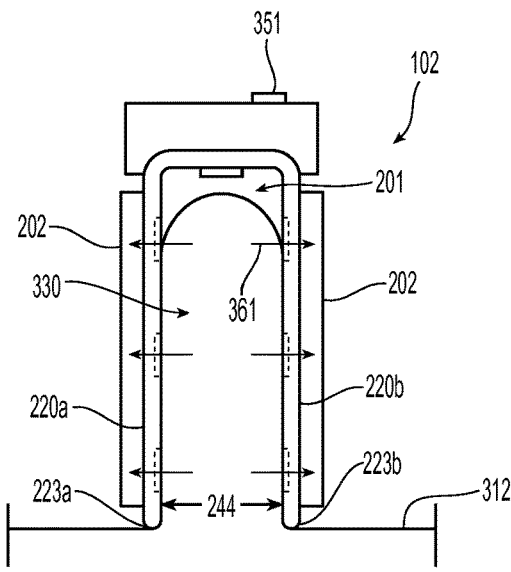
Figure 15:
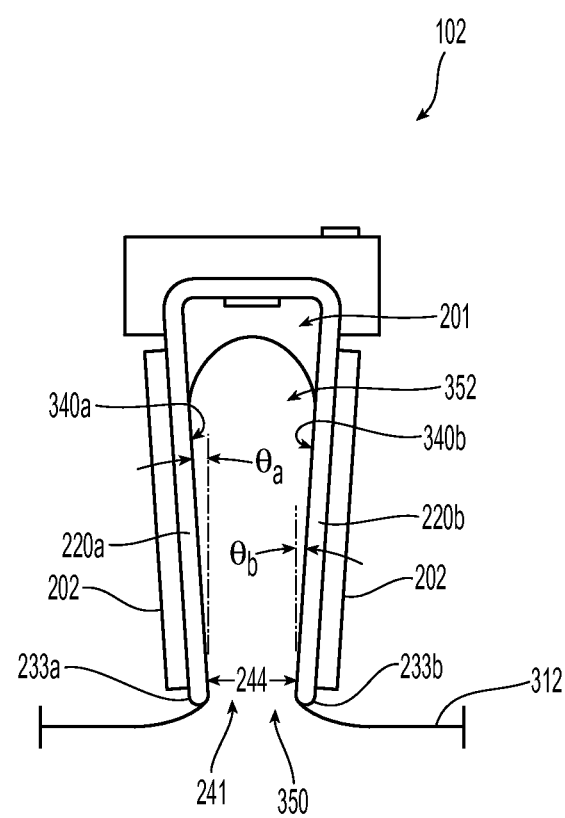

FIG. 12 shows the applicator 102 placed against the subject's skin 312. Although not shown in FIG. 12 for ease of illustration, other elements, materials, components (e.g., gel pads) can be used between the skin 312 and the applicator 102. U.S. Pub. No. 2007/0255362 and U.S. Patent Publication No. 2008/0077201 discloses components, materials (e.g., coupling gels, cryoprotectants, etc.), and elements (e.g., coupling devices, liners/protective sleeves, absorbents, etc.) that can used. Before, during, or after placement of the applicator 102, the applicator 102 is moved to a gentle tissue draw configuration with an oversized or enlarged opening 241 and/or gap 244. The vacuum port 230 can be used to produce a desired vacuum level in the cavity 201 to gently pull the subject's tissue toward the back 313 of the cavity 201. The width of the opening 241 (the width of gap 244) can be controllably increased or decreased to decrease or increase the stresses (e.g., shear stresses) produced in the subject's skin 312 associated with the drawing process. The draft angles $\beta_a$, $\beta_b$ can be increased to reduce mechanical stresses in the tissue so as to increase patient comfort as the subject's skin slides smoothly along the lip 226 and the interior surfaces of the applicator 102. In some cryotherapy procedures, the applicator 102 can define positive draft angles $\beta_a$, $\beta_b$ in a range of about 5 degrees to about 30 degrees such that tissue is drawn deep into the cavity 201 more comfortable than tissue being drawn into the applicator 102 in the treatment configuration (FIGS. 14 and 15). The positive draft angles $\beta_a$, $\beta_b$ can be selected based on the treatment site, desired volume of tissue to be drawn into the applicator 102, and/or desire vacuum level.

FIG. 13 shows the applicator 102 during the tissue draw process. The skin 312 and underlying tissue can be pulled away from the subject's body which can assist in cooling underlying tissue by, e.g., lengthening the distance between the subcutaneous fat and the relatively well-perfused muscle tissue and by allowing the underlying adipose tissue simultaneously to be cooled from two sides. The vacuum level can be increased or decreased to increase or decrease the tissue draw depth 320. In some embodiments, the tissue draw depth 320 can be equal to or greater than about 50%, 60%, 70%, 80%, or 90% of a depth 322 of the cavity 201. Other tissue draw depths can be achieved, if needed or desired.

FIG. 14 shows the applicator 102 in a narrowed configuration after the sidewalls 220a, 220b of FIG. 13 have been moved toward one another to compress the retained tissue 330. The lower ends or edges 223a, 223b of the sidewalls 220a, 220b closest to the subject's body have been moved to place the sidewalls 220a, 220b in a generally parallel configuration. The width of the gap 244 along the longitudinal length (length L in FIG. 6) of the tissue-receiving cavity 201 can be varying or generally constant. In some embodiments, the edges 223a, 223b can remain generally parallel when the sidewalls 220a, 220b are moved. In other embodiments, the edges 223a, 223b can be non-parallel to accommodate the subject's tissue. A sufficient vacuum can be maintained in the cavity 201 to keep most of the retained tissue 330 (e.g., at least about 70%, 80%, 90%, or 95% by volume of the retained tissue 330 of FIG. 13) within the cavity 201 during the tissue compression process. The narrowed configuration can provide high thermal contact with the tissue 330 to improve heat extraction from deeper tissue by, for example, reducing the heat transfer path length (e.g., path lengths from the thermal elements 202 to targeted tissue), reducing fluid content in the retained tissue 330, inhibiting warm blood perfusion into the retained tissue 330, or combinations thereof. In some embodiments, most or substantially all the volume of tissue 330 within the cavity 201 can be compressed with generally uniform pressure to promote uniform heat transfer along the retained tissue 330.

The control module 106 (FIG. 1) can automatically begin heating/cooling the tissue 330. In other embodiments, the control module 106 (FIG. 1) can notify the operator that the applicator 102 ready for treatment. FIG. 14 shows an indicator 351 that can provide an auditory alert and/or a visual alert when the applicator 102 is at the desired treatment configuration. The operator can inspect the applicator 102 and treatment site before beginning treatment.

To cool tissue 330, heat (represented by arrows with one arrow labeled 361) can be transferred from targeted tissue (e.g., epidermis, dermis, or subcutaneous tissue) to the thermal elements 202. The targeted tissue can be cooled to a temperature in a range from about −40° C. to about 10° C., from about −30° C. to about 10° C., from about −20° C. to about 10° C., from about 0° C. to about 20° C., from about −15° C. to about 5° C., from about −5° C. to about 15° C., or from about −10° C. to about 0° C. By cooling the subcutaneous tissue, for example, subcutaneous lipid-rich cells may be selectively reduced or damaged. As detailed above, because non-lipid-rich cells usually can withstand colder temperatures better than lipid-rich cells, the subcutaneous lipid-rich cells can be injured selectively while maintaining the non-lipid-rich cells (e.g., non-lipid-rich cells in the dermis and epidermis). To heat tissue, heat can travel in the opposite direction of the arrows. The configuration of the applicator 102 can be adjusted any number of times to, for example, keep tissue within the cavity 201 (i.e., to prevent applicator pop off), adjust the distance from the targeted tissue to the thermal elements 202, massage tissue, mechanically stress tissue, etc.

FIG. 15 shows the applicator 102 after the sidewalls 220a, 220b of FIG. 14 have been moved to compress the tissue 350 (e.g., tissue at a root of the tissue bulge) located in the entrance opening 241 more than tissue 352 located within a widened section of the cavity 201. The ends 233a, 233b of the sidewalls 220a, 220b can be generally parallel to one another, or at another desired orientation. Sufficient pressure can be applied to the tissue 350 to reduce, limit, or eliminate blood flow to the deeper tissue 352 to improve cooling efficiency because blood circulation is one mechanism for maintaining a constant body temperature of about 37° C. Blood flow through the dermis and subcutaneous layer of the tissue 350 is a heat source that counteracts the cooling of the targeted tissue (e.g., sub-dermal fat). If the blood flow is not reduced, cooling the subcutaneous tissues would require not only removing the specific heat of the tissues but also that of the blood circulating through the tissues. Thus, reducing or eliminating blood flow through the tissue 352 can improve the efficiency of cooling and avoid excessive heat loss from the dermis and epidermis. In some embodiments, the applicator 102 applies a pressure greater than or equal to systolic blood pressure in the skin. The clamping force, for example, applied to the tissue 350 can be higher than the systolic pressure to impede or block the blood flow into and through the deeper issue 352 before, during, and/or after cooling.

The surfaces 340a, 340b of the sidewalls 220a, 220b, respectively, can define negative draft angles $\theta_a$, $\theta_b$ for enhanced gripping of the tissue 352. To pull the applicator 102 off the patient, the wider portion of the tissue 352 located deep in the cavity 201 must be pulled through the relatively narrow entrance opening 241. Even if the vacuum level is reduced or the vacuum is stopped, the applicator 102 can securely grip the tissue to avoid a "pop off" event. In some embodiments, the negative draft angles $\theta_a$, $\theta_b$ can be equal to or greater than about 5 degrees, 10 degrees, 15 degrees, 20 degrees, or 30 degrees. Other negative draft angles can be used, if needed or desired. Additionally, when the applicator 102 is reconfigured to define the negative draft angles, tissue can be urged deeper into the cavity 201. As such, a lower vacuum level can be used to obtain a relatively deep draw. In some embodiments, the thermal elements 202 can be planar and have a rigid construction to help push the tissue deep into the cavity 201. In other embodiments, the thermal elements 202 can be non-planar and conformable to provide a high level of tissue contact.

It will be appreciated that while a region of the body has been cooled or heated to the target temperature, in actuality that region of the body may be close but not equal to the target temperature, e.g., because of the body's natural heating and cooling variations. Thus, although the applicator 102 may attempt to heat or cool the tissue to the target temperature or to provide a target heat flux, the sensors 302 (FIG. 6) may measure a sufficiently close temperature or heat flux. If the target temperature has not been reached, operation of the thermal elements 202 can be adjusted to change the heat flux to maintain the target temperature or "set-point" selectively to affect targeted tissue. When the prescribed segment duration expires, the next treatment profile segment can be performed.

FIGS. 12-15 are simplified views that do not show features that can be used for cryotherapy. Cryoprotectant can be used with the applicator 102 and can be carried by cotton and/or gauze material. In one embodiment, a cryoprotectant element positionable between the thermal elements 202 and the subjects tissue 312 is a cotton pad preloaded with cryoprotectant. The cryoprotectant can be freezing point temperature depressant that may additionally include a thickening agent, a pH buffer, a humectant, a surfactant, and/or other additives. The temperature depressant may include, for example, polypropylene glycol (PPG), polyethylene glycol (PEG), dimethyl sulfoxide (DMSO), or other suitable alcohol compounds. In a particular embodiment, a cryoprotectant may include about 30% polypropylene glycol, about 30% glycerin (a humectant), and about 40% ethanol. In another embodiment, a cryoprotectant may include about 40% propylene glycol, about 0.8% hydroxyethylcellulose (a thickening agent), and about 59.2% water. In a further embodiment, a cryoprotectant may include about 50% polypropylene glycol, about 40% glycerin, and about 10% ethanol. Other cryoprotectants or agents can also be used.

In some embodiments, a protective liner (not shown) can prevent direct contact between the applicator 102 and the subject's skin to reduce the likelihood of cross-contamination between patients, minimize cleaning requirements for the applicator 102, etc. The protective liner can be a sheet, a sleeve, or other component constructed from latex, rubber, nylon, Kevlar®, or other substantially impermeable or semipermeable material. Further details regarding a patient protection device may be found in U.S. Patent Publication No. 2008/0077201. A liner or protective sleeve may be positioned between the absorbent and the applicator 102 to shield the applicator 102 and to provide a sanitary barrier that is, in some embodiments, inexpensive and thus disposable.

Figure 16:
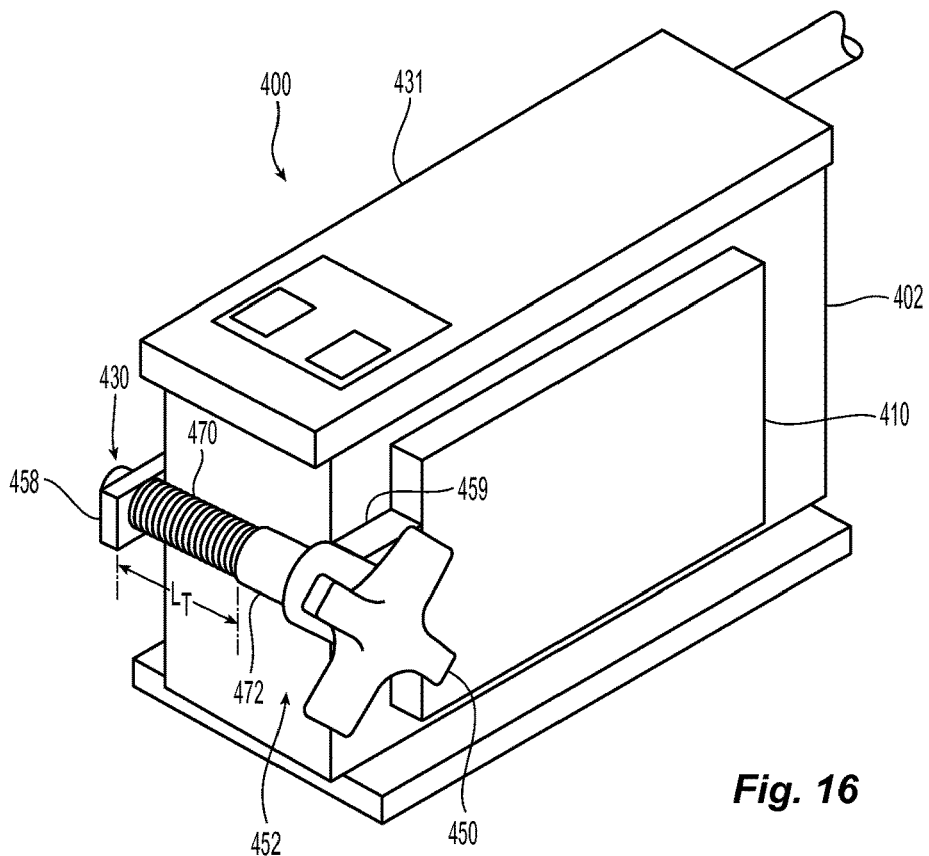
FIGS. 16 and 17 are isometric views of a manually adjustable gap applicator in accordance with an embodiment of the technology.

FIG. 16 is an isometric view of an adjustable gap applicator 400 in accordance with embodiments of the technology. The applicator 400 is generally similar to the applicator 102 discussed in connection with FIGS. 1-15 and can generally include a vacuum cup 402, one or more thermal elements 410, and an adjustment mechanism 430. The adjustment mechanism 430 can reconfigure the vacuum applicator 400 and can have an expansion mode for enlargement of a tissue-receiving gap or cavity and a contraction mode for compressing tissue.

In some embodiments, the adjustment mechanism 430 includes a drive device 452 and connectors 458, 459. The drive device 452 can be a screw drive assembly having a knob 450 and an externally threaded member 470. The threaded member 470 engages internal threads of the connector 458 and is freely rotatable relative to the connector 459. The connector 458 can be coupled to one side of the vacuum cup 402 and/or thermal elements 410, and the connector 459 can be coupled to an opposing side of the vacuum cup 402 and/or thermal element (not shown). The knob 450 can be manually rotated clockwise to drive the connectors 458, 459 toward one another and manually rotated counterclockwise to drive the connectors 458, 459 away from one another.

Figure 17:
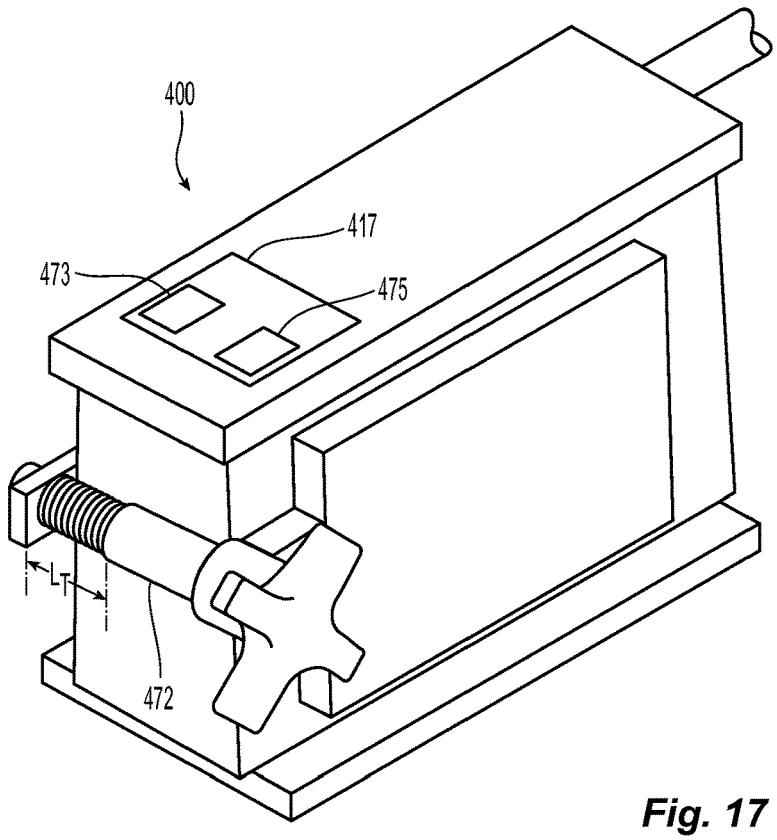

The adjustable gap applicator 400 can also include a gap limiter 472. In some manually operated embodiments, the gap limiter 472 can be manually rotated to move it axially along the threaded member 470. As shown in FIGS. 16 and 17, the gap limiter 472 can be adjusted to set the maximum length of travel $L_T$, thus setting the minimum size of the tissue-receiving cavity or gap. By way of example, FIG. 17 shows the gap limiter 472 positioned to reduce the length of travel $L_T$ compared to the length of travel $L_T$ shown in FIG. 16. In some automated embodiments, the gap limiter 472 can include a drive mechanism for moving between different positions. The applicator 102 discussed in connection with FIGS. 1-15 can also have a gap limiter.

FIG. 17 shows a control panel 417 that can provide the operator with the ability to control and/or monitor treatment. For example, a first ON/OFF button 473 may toggle the initiation or termination of a treatment and a second ON/OFF button 475 may actuate a pump (e.g., pressurization device 117 of FIG. 1) for drawing a vacuum in the interior cavity. Indicator lights may provide a visual indication of, for example, whether the adjustable gap applicator 400 is at a desired configuration, whether a treatment is proceeding, and/or whether the vacuum level is achieved.

Figure 18:
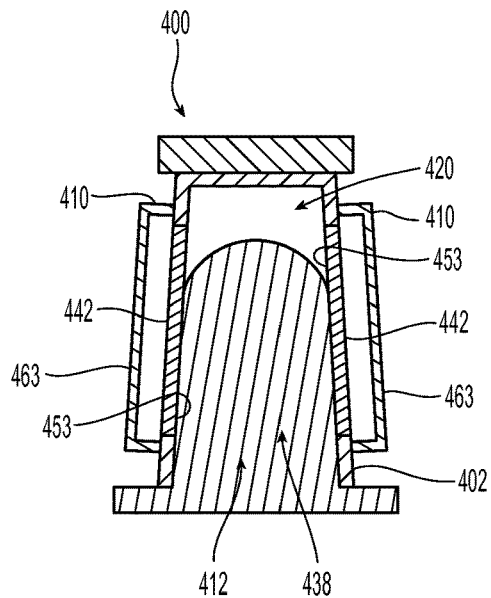
FIGS. 18-20 are a series of schematic views of the applicator of FIGS. 16 and 17 in different configurations.
Figure 19:
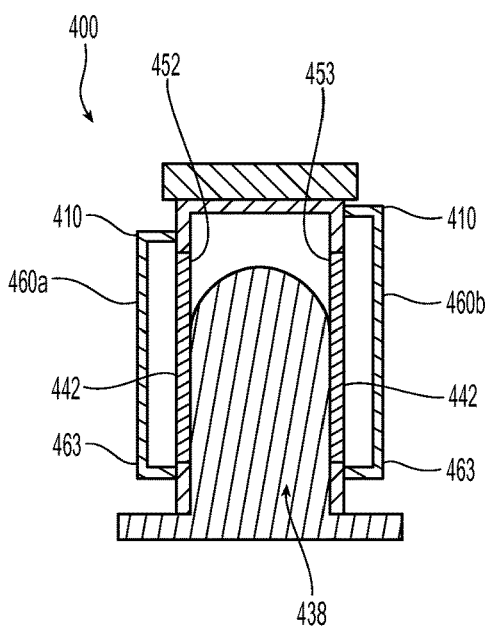
Figure 20:
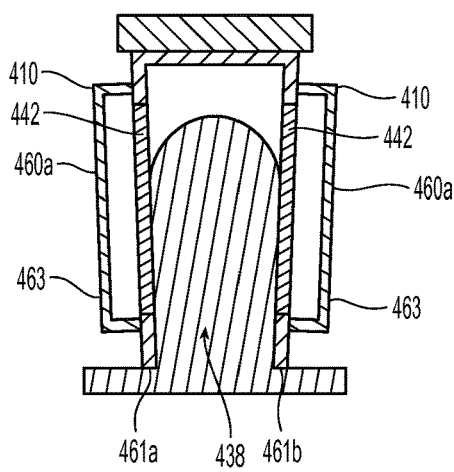

FIGS. 18-20 are a series of views of a method of performing cryotherapy using the applicator 400 in accordance with various embodiments of the present technology. Generally, heat can be transferred from targeted tissue to cooling plates 442 of the thermal elements 410 to cool tissue 438. To heat tissue 438, heat can travel in the opposite direction. The thermal elements 410 can include protective covers 463 coupled to the vacuum cup 402. Details of the operation of the applicator 400 are discussed below.

FIG. 18 is a cross-sectional view of the applicator 400 in an expanded or a tissue-draw configuration with tissue held in the cavity 420. The cooling plates 442 can be at a slightly open arrangement (e.g., inner surfaces 453 of the cooling plates 442 can define positive draft angles). FIG. 19 shows the applicator 400 after the sidewalls 460a, 460b have been moved toward each other, and the inner surfaces 453 are generally parallel to one another. FIG. 20 shows the applicator 400 after the sidewalls 460a, 460b have been moved further toward each to define negative draft angles. Ends 461a, 461b of the sidewalls 460a, 460b can extend in a direction perpendicular to the width of the gap 412 and can be generally parallel to one other.

Figure 21:
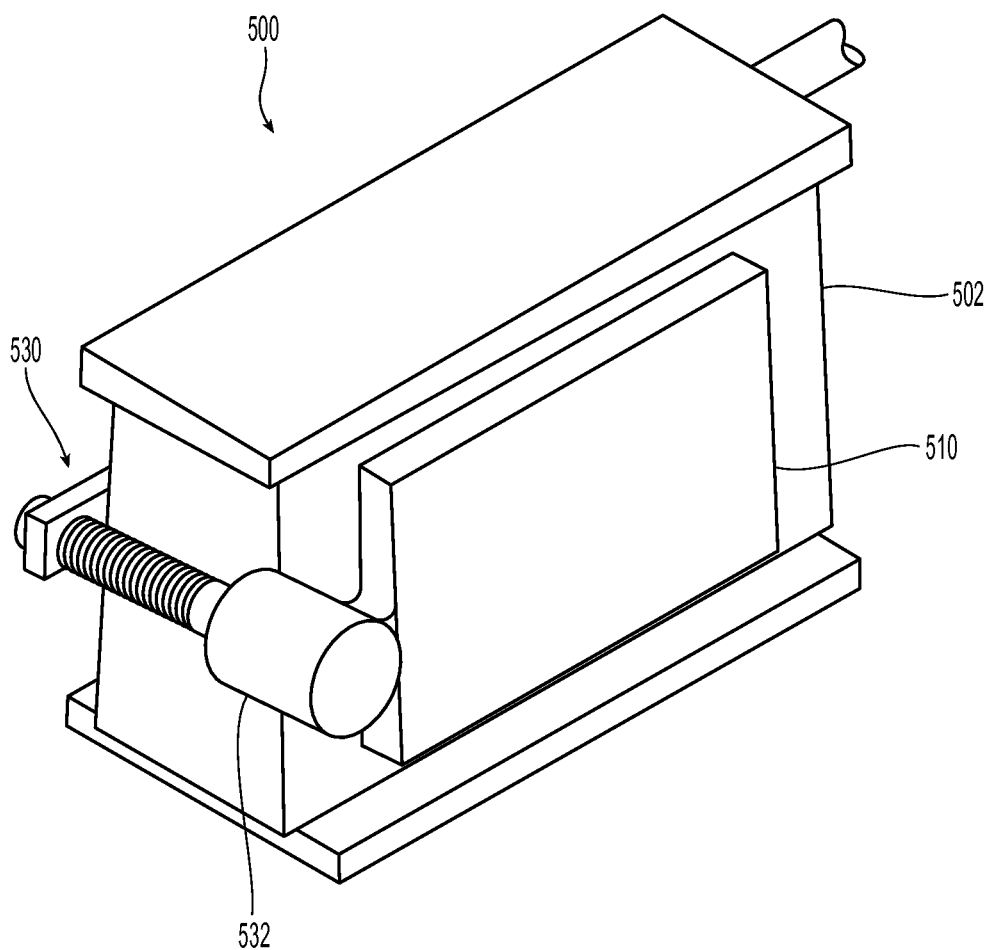
FIG. 21 is an isometric view of a motorized adjustable gap applicator in accordance with an embodiment of the technology.

FIG. 21 is an isometric view of an applicator 500 in accordance with embodiments of the technology. The applicator 500 can generally include a vacuum cup 502, one or more thermal elements 510, and an adjustment mechanism 530. The adjustment mechanism 530 can automatically reconfigure the vacuum cup 502 and can include a drive device 532 (e.g., a motor). In an expansion mode, the adjustment mechanism 530 can enlarge the tissue-receiving cavity, and in contraction mode, the applicator 500 can reduce the size of the cavity. The applicator 500 can include a manually adjustable gap limiter or other type of gap limiter.

Figure 22:
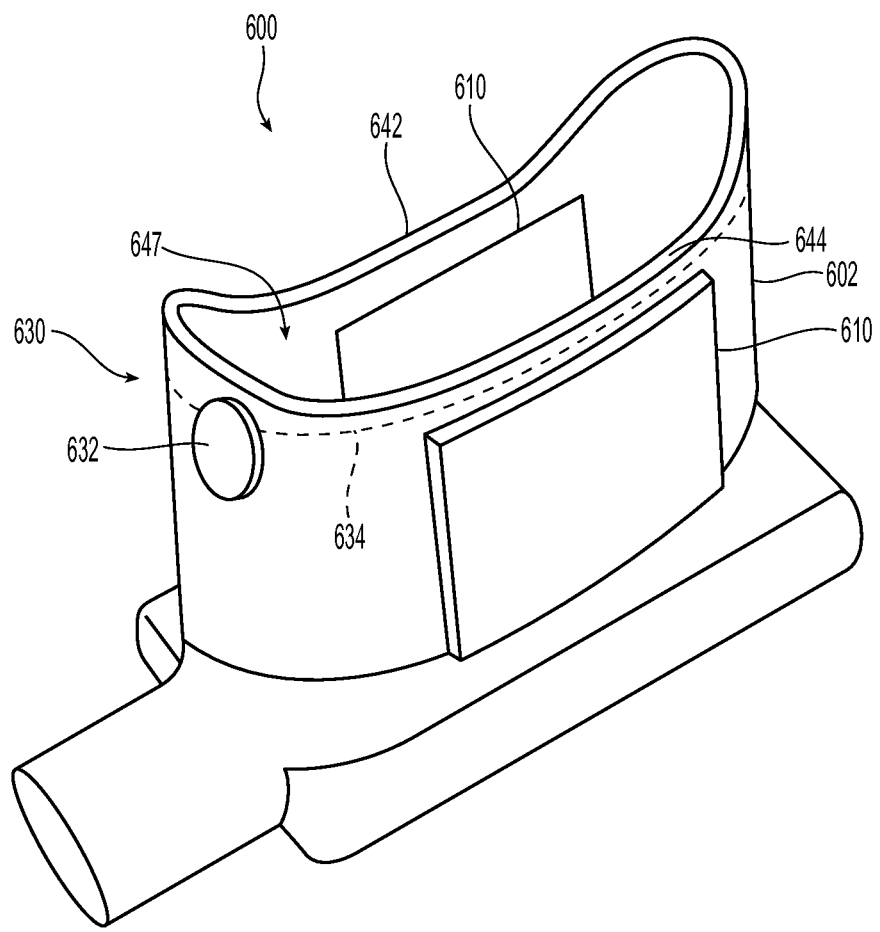
FIG. 22 is an isometric view of an adjustable gap applicator in accordance with another embodiment of the technology.

FIG. 22 is an isometric view of an applicator 600 in accordance with embodiments of the technology. The applicator 600 can generally include a vacuum cup 602, one or more thermal elements 610, and an adjustment mechanism 630. The adjustment mechanism 630 can include a control element 632 and a tensioner 634 (shown in phantom line). The control element 632 can include a dial, a ratchet mechanism, or the like and can be used to increase or decrease the tension in the tensioner 634 to controllably move the sidewalls 642, 644, or other features of the applicator 600. The tensioner 634 can include one or more cables, wires, or other flexible elongate members that can pass through a passageway in the vacuum cup 602. In other embodiments, the tensioner 634 can extend through guides (e.g., eyelets, rings, etc.) connected to the vacuum cup 602. Exemplary ratchet mechanisms (e.g., reels), tensioners, and methods of tensioning are described in, e.g., U.S. Pat. Nos. 8,516,662 and 7,591,050, which are incorporated by reference in their entireties.

In some embodiments, the control element 632 can be used to gradually increase the tension in the tensioner 634 to pull the sidewalls 642, 644 inwardly to narrower or close an entrance opening 647. To widen or open the entrance opening 647, the control element 632 can be used to reduce the tension in the tensioner 634. The bias provided by the vacuum cup 602 can cause widening or opening of the entrance opening 647.

Exemplary components, cryoprotectants, and features that can be used with and/or incorporated into the applicators disclosed herein are described in, e.g., commonly assigned U.S. Pat. No. 7,854,754; U.S. patent application Ser. No. 14/610,807; and U.S. Patent Publication Nos. 2008/0077201, 2008/0077211, 2008/0287839, 2011/0238050 and 2011/0238051. In further embodiments, the treatment systems disclosed herein may also include a patient protection device (not shown) incorporated into the applicators to prevent directed contact between the applicator and a patient's skin and thereby reducing the likelihood of cross-contamination between patients, minimizing cleaning requirements for the applicator. The patient protection device may also include or incorporate various storage, computing, and communications devices, such as a radio frequency identification (RFID) component, allowing for example, use to be monitored and/or metered. Exemplary patient protection devices are described in commonly assigned U.S. Patent Publication No. 2008/0077201.

Although noninvasive applicators are illustrated and discussed with respect to FIGS. 1-22, minimally invasive applicators may also be employed. As an example, a cryoprobe, electrode, and/or other invasive component may be incorporated into the applicators disclosed herein and can be inserted directly into the targeted tissue (e.g., subcutaneous adipose tissue) to cool, freeze, or otherwise thermally process the targeted tissue. Applicators disclosed herein can also include elements (e.g., electrodes, vibrators, etc.) for delivering energy, such as radiofrequency energy, ultrasound energy (e.g., low frequency ultrasound, high frequency ultrasound, etc.), mechanical massage, and/or electric fields. The energy can be selected to affect treatment by, for example, heating tissue. Additionally, or alternatively, energy can be used to affect the crystal formation in non-targeted tissues while allowing cooling of the targeted tissue. In non-targeted cells or structures, non-thermal energy parameters may be selected to reduce ice crystal size and/or length, reduce freezing lethality, or the like. In targeted cells or structures, non-thermal energy parameters may be selected to enhance crystal nucleation. Thus, energy can be selectively applied to control therapy. The treatment systems disclosed herein may be used with a substance that may provide a thermal coupling between the subject's skin and the thermal element(s) to improve heat transfer therebetween. The substance may be a fluid, a liquid, a gel, or a paste, which may be hygroscopic, thermally conductive, and biocompatible.

E. Computing Environments

Figure 23:
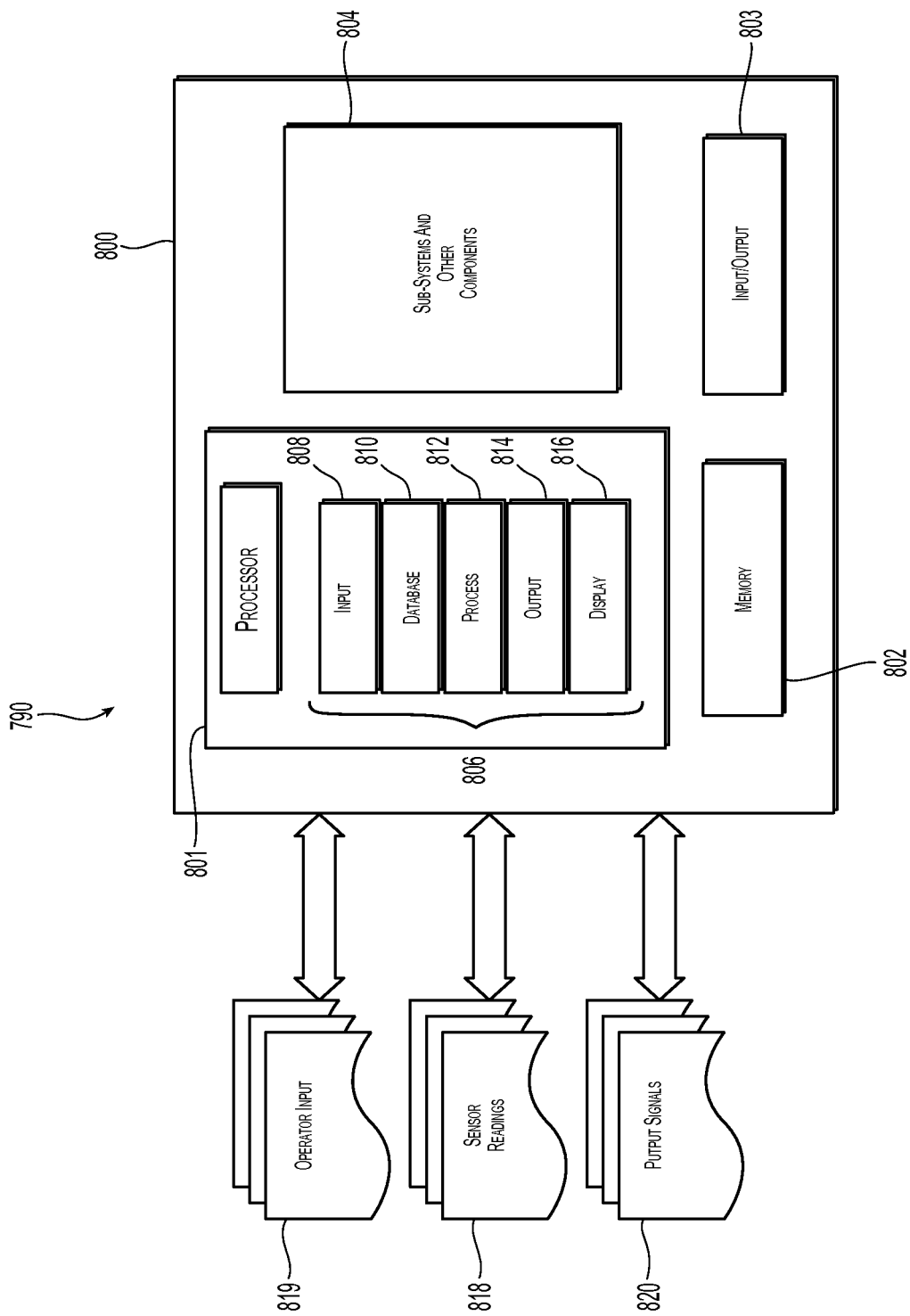
FIG. 23 is a schematic block diagram illustrating subcomponents of a controller in accordance with an embodiment of the technology.

FIG. 23 is a schematic block diagram illustrating subcomponents of a controller in accordance with an embodiment of the disclosure. The controller 790 can be the controller 114 of FIG. 1 or can be incorporated into the applicators disclosed herein. The controller 790 can include a computing device 800 having a processor 801, a memory 802, input/output devices 803, and/or subsystems and other components 804. The computing device 800 can perform any of a wide variety of computing processing, storage, sensing, imaging, and/or other functions. Components of the computing device 800 may be housed in a single unit or distributed over multiple, interconnected units (e.g., though a communications network). The components of the computing device 800 can accordingly include local and/or remote memory storage devices and any of a wide variety of computer-readable media.

As illustrated in FIG. 23, the processor 801 can include a plurality of functional modules 806, such as software modules, for execution by the processor 801. The various implementations of source code (i.e., in a conventional programming language) can be stored on a computer-readable storage medium or can be embodied on a transmission medium in a carrier wave. The modules 806 of the processor can include an input module 808, a database module 810, a process module 812, an output module 814, and, optionally, a display module 816.

In operation, the input module 808 accepts an operator input 819 via the one or more input devices, and communicates the accepted information or selections to other components for further processing. The database module 810 organizes records, including patient records, treatment data sets, treatment profiles and operating records and other operator activities, and facilitates storing and retrieving of these records to and from a data storage device (e.g., internal memory 802, an external database, etc.). Any type of database organization can be utilized, including a flat file system, hierarchical database, relational database, distributed database, etc.

In the illustrated example, the process module 812 can generate control variables based on sensor readings 818 from sensors (e.g., sensors 302 of FIG. 6) and/or other data sources, and the output module 814 can communicate operator input to external computing devices and control variables to the controller. The display module 816 can be configured to convert and transmit processing parameters, sensor readings 818, output signals 820, input data, treatment profiles and prescribed operational parameters through one or more connected display devices, such as a display screen, printer, speaker system, etc.

In various embodiments, the processor 801 can be a standard central processing unit or a secure processor. Secure processors can be special-purpose processors (e.g., reduced instruction set processor) that can withstand sophisticated attacks that attempt to extract data or programming logic. The secure processors may not have debugging pins that enable an external debugger to monitor the secure processor's execution or registers. In other embodiments, the system may employ a secure field programmable gate array, a smartcard, or other secure devices.

The memory 802 can be standard memory, secure memory, or a combination of both memory types. By employing a secure processor and/or secure memory, the system can ensure that data and instructions are both highly secure and sensitive operations such as decryption are shielded from observation. In various embodiments, the memory 802 can be flash memory, secure serial EEPROM, secure field programmable gate array, or secure application-specific integrated circuit.

The input/output device 118 can include, without limitation, a keyboard, a mouse, a stylus, a push button, a switch, a potentiometer, a scanner, an audio component such as a microphone, or any other device suitable for accepting user input and can also include one or more video monitor, a medium reader, an audio device such as a speaker, any combination thereof, and any other device or devices suitable for providing user feedback. For example, if the applicator 113 moves an undesirable amount during a treatment session, the input/output device 803 can alert the subject 101 and/or operator via an audible alarm. The input/output device 118 can be a touch screen that functions as both an input device and an output device. The control panel can include visual indicator devices or controls (e.g., indicator lights, numerical displays, etc.) and/or audio indicator devices or controls. The control panel may be a component separate from the input/output device 118 and/or output device 120, may be integrated with one or more of the devices, may be partially integrated with one or more of the devices, may be in another location, and so on. In alternative embodiments, the controller 114 can be contained in, attached to, or integrated with the applicator 113. In yet other embodiments, the various components can be fixedly installed at a treatment site. Further details with respect to components and/or operation of applicators, control modules (e.g., treatment units), and other components may be found in commonly-assigned U.S. Patent Publication No. 2008/0287839.

The controller 790 can include any processor, Programmable Logic Controller, Distributed Control System, secure processor, and the like. A secure processor can be implemented as an integrated circuit with access-controlled physical interfaces; tamper resistant containment; means of detecting and responding to physical tampering; secure storage; and shielded execution of computer-executable instructions. Some secure processors also provide cryptographic accelerator circuitry. Suitable computing environments and other computing devices and user interfaces are described in commonly assigned U.S. Pat. No. 8,275,442, entitled "TREATMENT PLANNING SYSTEMS AND METHODS FOR BODY CONTOURING APPLICATIONS," which is incorporated herein in its entirety by reference.

The controller 790 can store, determine, and/or monitor thermal cycles for sequentially cooling and heating a treatment site any number of times. The controller 790 can select the order and lengths of thermal cycles (e.g., heating cycles, cooling cycles, etc.), target parameters (e.g., temperatures, temperature ranges, etc.), and/or temperature profiles. In some procedures, a treatment site can be cooled/heated to keep tissue at a temperature below 37° C. (e.g., a temperature between about 10° C. to about 35° C., between about 15° C. to about 35° C., between about 10° C. to about 30° C., between about 20° C. to about 35° C., or between about 15° C. to about 20° C., etc.). The tissue can be kept at a temperature (or in a temperature range) for a period of time equal to or shorter than about 1 minute, about 2 minutes, about 2.3 minutes, about 3 minutes, about 5 minutes, or other suitable period of time. The treatment site can then be cooled to a lower temperature (e.g., a temperature equal to or lower than about 10° C., about 2° C., about −5° C., about −10° C., about −13° C., about −20° C., about −30° C., etc.) for a cooling period equal to or longer than about 20 minutes, about 30 minutes, about 40 minutes, about 50 minutes, about 1 hour, about 70 minutes, about 80 minutes, about 90 minutes, or other suitable time period.

After cooling, an applicator can be actively or passively warmed to room temperature, skin temperature, or other suitable temperature. For example, the thermoelectric elements of the applicator can be passively (e.g., naturally) returned to room temperature prior to removing the applicator from the subject. After removing the applicator, the treatment site can be massaged. The period of heating can be equal to or less than about 5 minutes, about 10 minutes, or about 20 minutes. The length of the total treatment session can be equal or greater than about 30 minutes, about 40 minutes, about 50 minutes, about 1 hour, 1.5 hours, 2 hours, or 3 hours, etc.

In one procedure, an initial thermal routine can be performed to preheat tissue or to keep the tissue at a temperature that prepares the treatment site for a cooling routine. For example, the tissue can be kept at a temperature of about 30° C. for a period of time (e.g., 2.3 minutes). The tissue is then cooled to a temperature of about −13° C. for about 70 minutes. Cooling surfaces of the applicator can then return to room temperature (e.g., 22° C.) naturally before a clinician starts a massage process. In other procedures, the tissue is initially heated to a high temperature (e.g., 40° C., 45° C., etc.) for a first period of time (e.g., 3 minutes, 5 minutes, 10 minutes, etc.). The tissue is then cooled to a lower temperature (e.g., −30° C., −15° C., 5° C., 10° C., 15° C., 20° C., etc.) for a second period of time (e.g., 20 minutes, 30 minutes, 40 minutes, 50 minutes, etc.). The tissue is then warmed to a temperature (e.g., 20° C., 30° C., 35° C., 40° C., 45° C., etc.) for a third period of time (e.g., 20 minutes, 30 minutes, 40 minutes, 50 minutes, etc.). Other temperatures and treatment times can be selected based on the treatment.

The applicators in some embodiments can deliver energy (e.g., radiofrequency energy, ultrasound energy, etc.) to and remove heat from the target region. A session may have a single stage of delivering energy that ceases prior to a single stage of removing heat from target tissue. Additionally, sequential application of the stages of heating or cooling may occur multiple times so that multiple non-overlapping stages of energy delivery and heat removal occur. For example, thermal elements of an applicator can perform a heating cycle while other thermal elements of the applicator perform a cooling cycle. The controller 790 can store various executable programs for controlling applicators disclosed herein to perform a wide range of thermal cycles for body contouring, treating cellulite, improving skin appearance, targeting glands, and/or performing other methods as described in, for example, U.S. patent application Ser. No. 14/611,127 entitled "TREATMENT SYSTEMS, METHODS, AND APPARATUS FOR IMPROVING THE APPEARANCE OF SKIN AND PROVIDING FOR OTHER TREATMENTS, U.S. patent application Ser. No. 14/611,052 entitled "TREATMENT SYSTEMS AND METHODS FOR TREATING CELLULITE AND FOR PROVIDING OTHER TREATMENTS," and International Patent Application No. PCT/US2015/013,971 entitled "TREATMENT SYSTEMS AND METHODS FOR AFFECTING GLANDS AND OTHER TARGETED STRUCTURES," which are incorporated herein in their entireties by reference.

F. Conclusion

Various embodiments of the technology are described above. It will be appreciated that details set forth above are provided to describe the embodiments in a manner sufficient to enable a person skilled in the relevant art to make and use the disclosed embodiments. Several of the details and advantages, however, may not be necessary to practice some embodiments. Additionally, some well-known structures or functions may not be shown or described in detail, so as to avoid unnecessarily obscuring the relevant description of the various embodiments. Although some embodiments may be within the scope of the technology, they may not be described in detail with respect to the Figures. Furthermore, features, structures, or characteristics of various embodiments may be combined in any suitable manner. For example, features of the applicator 102 can be incorporated into the applicators 400, 500, 600. Moreover, one skilled in the art will recognize that there are a number of other technologies that could be used to perform functions similar to those described above. While processes or blocks are presented in a given order, alternative embodiments may perform routines having stages, or employ systems having blocks, in a different order, and some processes or blocks may be deleted, moved, added, subdivided, combined, and/or modified. Each of these processes or blocks may be implemented in a variety of different ways. Also, while processes or blocks are at times shown as being performed in series, these processes or blocks may instead be performed in parallel, or may be performed at different times. The headings provided herein are for convenience only and do not interpret the scope or meaning of the described technology.

Unless the context clearly requires otherwise, throughout the description, the words "comprise," "comprising," and the like are to be construed in an inclusive sense as opposed to an exclusive or exhaustive sense; that is to say, in a sense of "including, but not limited to." Words using the singular or plural number also include the plural or singular number, respectively. Use of the word "or" in reference to a list of two or more items covers all of the following interpretations of the word: any of the items in the list, all of the items in the list, and any combination of the items in the list. Furthermore, the phrase "at least one of A, B, and C, etc." is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.).

Any patents, applications and other references, including any that may be listed in accompanying filing papers, are incorporated herein by reference. Aspects of the described technology can be modified, if necessary, to employ the systems, functions, and concepts of the various references described above to provide yet further embodiments. These and other changes can be made in light of the above Detailed Description. While the above description details certain embodiments and describes the best mode contemplated, no matter how detailed, various changes can be made. Implementation details may vary considerably, while still being encompassed by the technology disclosed herein. As noted above, particular terminology used when describing certain features or aspects of the technology should not be taken to imply that the terminology is being redefined herein to be restricted to any specific characteristics, features, or aspects of the technology with which that terminology is associated.

What is claimed is:

1. A system for treating a subject, the system comprising:
   a vacuum applicator configured to receive the subject's tissue, the vacuum applicator including
      a base,
      a first sidewall and a second sidewall, wherein the base and the first and the second sidewalls at least partially define a tissue-receiving cavity, wherein the first and the second sidewalls at least partially define an entrance opening opposite the base, and wherein a first width is defined between the first and the second sidewalls at the entrance opening and a second width is defined between the first and the second sidewalls at the base,
      a vacuum port that provides a vacuum to draw the subject's tissue into the tissue-receiving cavity,
      a thermal element configured for heat transfer with the subject's tissue that has been drawn into the tissue-receiving cavity to affect the tissue, and
      a cavity adjustment mechanism having an expansion mode and a contraction mode,
         wherein the cavity adjustment mechanism in the expansion mode widens the tissue-receiving cavity to an expanded gentle tissue draw configuration, and
         wherein the cavity adjustment mechanism in the contraction mode translates and rotates the first and the second sidewalls toward one another such that the first width is smaller than the second width and the tissue-receiving cavity narrows to compress the subject's tissue located at the entrance opening of the tissue-receiving cavity to (a) urge the subject's tissue deeper into the tissue-receiving cavity, (b) increase thermal contact between the thermal element and the subject's tissue that has been drawn into the tissue-receiving cavity, and (c) pinch a root of the subject's tissue that has been drawn into the tissue-receiving cavity to reduce blood flow to the subject's tissue that has been drawn into the tissue-receiving cavity; and
- a tissue draw depth detector that detects a depth of the subject's tissue that has been drawn into the tissue-receiving cavity; and
- a controller in communication with the vacuum applicator and containing instructions for switching the cavity adjustment mechanism between the expansion mode and the contraction mode.

2. The system of claim 1 wherein the first sidewall and the second sidewall are located on opposite sides of the tissue-receiving cavity.

3. The system of claim 1 wherein the vacuum applicator is configured to compress the subject's tissue held in the tissue-receiving cavity when the tissue-receiving cavity moves from the gentle tissue draw configuration to a narrowed configuration.

4. The system of claim 1, wherein the vacuum port is positioned to provide sufficient vacuum to keep most of a volume of the subject's tissue within the tissue-receiving cavity while the cavity adjustment mechanism narrows the tissue-receiving cavity.

5. The system of claim 1 wherein the cavity adjustment mechanism in the contraction mode narrows the tissue-receiving cavity to reduce a width of the tissue-receiving cavity by at least about 10%.

6. The system of claim 1, further comprising a pressurization device in fluid communication with the vacuum port, and wherein the controller contains stored instructions executable by the controller to command the system to draw the subject's tissue into the tissue-receiving cavity using a vacuum generated by the pressurization device.

7. The system of claim 1 wherein the tissue draw depth detector is configured to detect when a sufficient volume of the subject's tissue has been drawn into the tissue-receiving cavity, and wherein the tissue draw depth detector includes one or more sensors.

8. The system of claim 7 wherein the tissue draw depth detector includes one or more contact sensors, air volume sensors, optical depth sensors, and/or imaging devices.

9. The system of claim 1 wherein at least one of the first and second sidewalls defines a positive draft angle when the tissue-receiving cavity is in the gentle tissue draw configuration.

10. The system of claim 1 wherein the tissue-receiving cavity in the gentle tissue draw configuration has a preset first volume, and wherein the tissue-receiving cavity in a high thermal contact configuration has a preset second volume that is less than the preset first volume.

11. The system of claim 1, wherein the vacuum applicator is configured to automatically start the contraction mode to move the opposing sides of the vacuum applicator toward the negative draft angles, thereby urging the subject's tissue deeper into the tissue-receiving cavity.

12. The system of claim 1, wherein the vacuum applicator includes a flexible mouth that surrounds the entrance to maintain an air-tight seal with the subject's skin while opposing lips of the flexible mouth move toward one another to push the subject's tissue deeper into the tissue-receiving cavity.

13. The system of claim 1 wherein the cavity adjustment mechanism in the contraction mode (a) translates and rotates the first sidewall toward the second sidewall and (b) translates and rotates the second sidewall toward the first sidewall.

14. The system of claim 1 wherein the tissue-receiving cavity includes a proximal tissue-receiving cavity portion adjacent the base and a distal tissue-receiving cavity portion adjacent the entrance opening, and
- wherein during the expansion mode the proximal tissue-receiving cavity portion has a volume smaller than or equal to a volume of the distal tissue-receiving cavity portion, and
- wherein during the contraction mode the volume of the proximal tissue-receiving cavity portion is larger than the volume of the distal tissue-receiving cavity portion.

15. A system for treating tissue of a subject, the system comprising:
- a vacuum applicator configured to receive the subject's tissue, the vacuum applicator including
  - a vacuum cup having a bottom,
  - a tissue-receiving gap,
  - at least one thermal element configured for heat transfer with the subject's tissue that has been drawn into the vacuum cup and the tissue-receiving gap to affect the subject's tissue, and
  - an entrance opening opposite the bottom of the vacuum cup that narrows to compress the subject's tissue located in the entrance opening more than the subject's tissue that has been drawn through the entrance opening and into the tissue-receiving gap between opposing sidewalls of the vacuum applicator, wherein the opposing sidewalls are configured to rotate toward one another such that a width of the tissue-receiving gap increases from the entrance opening toward the bottom of the vacuum cup and pinch a root of the subject's tissue proximate the entrance opening.

16. The system of claim 15, further comprising an adjustment mechanism operable to reconfigure the vacuum applicator to mechanically urge the subject's tissue deeper into the tissue-receiving gap.

17. The system of claim 16 wherein the adjustment mechanism has an expansion mode for enlarging a width of the tissue-receiving gap and a contraction mode for reducing the width of the tissue-receiving gap.

18. The system of claim 15 wherein the sidewalls include a first sidewall and a second sidewall located on opposite sides of the tissue-receiving gap, wherein at least one of the first and second sidewalls defines a positive draft angle for drawing the subject's tissue into the tissue-receiving gap.

19. The system of claim 15 wherein the at least one thermal element includes a first thermal element and a second thermal element, wherein the system further comprises an adjustment mechanism configured to move the first and second thermal elements relative to one another.

20. The system of claim 19, further including a controller in communication with the vacuum applicator and containing instructions for commanding an adjustment mechanism that controllably widens and narrows the tissue-receiving gap.

21. The system of claim 15, wherein the vacuum applicator is configured to controllably adjust the negative draft angle and a width of the tissue-receiving gap based on a position of the tissue with the vacuum cup, wherein the position is detected by the vacuum applicator.

22. A method for treating tissue of a subject, the method comprising:

drawing tissue of the subject into a vacuum applicator through an entrance opening and toward a bottom opposite the entrance opening in an expanded configuration using a vacuum;

moving the vacuum applicator from the expanded configuration to a narrowed treatment configuration such that opposing sides of a flexible mouth of the vacuum applicator translate and rotate toward one another to urge the subject's tissue deeper into the vacuum applicator and pinch a root of the subject's tissue drawn into the vacuum applicator while maintaining an air-tight seal between lips of the flexible mouth, encompassing the subject's tissue, and the subject's skin, thereby holding the subject's tissue within the vacuum applicator, wherein during the narrowed treatment configuration a first width between the opposing sides of the flexible mouth at the entrance opening is smaller than a second width between the opposing sides of the flexible mouth proximate to the bottom of the vacuum applicator; and transferring heat between the vacuum applicator and the subject's tissue held within the vacuum applicator in the narrowed treatment configuration.

23. The method of claim 22 wherein moving the vacuum applicator from the expanded configuration to the narrowed treatment configuration includes reducing a width of a tissue-receiving gap defined by the vacuum applicator a predetermined amount.

24. The method of claim 23 wherein the width of a tissue-receiving gap is reduced by at least about 10%.

25. The method of claim 22 wherein the subject's tissue is held within a tissue-receiving gap that is between two cooling plates of the vacuum applicator.

* * * * *